United States Patent
Lee et al.

(10) Patent No.: US 9,241,113 B2
(45) Date of Patent: Jan. 19, 2016

(54) APPARATUS AND METHOD FOR DISPLAYING IMAGES

(71) Applicant: SAMSUNG ELECTRONICS CO., LTD., Suwon-si (KR)

(72) Inventors: Young Joo Lee, Seoul (KR); Sung Nam Park, Yongin-si (KR); Jae Young Eum, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/167,348

(22) Filed: Jan. 29, 2014

(65) Prior Publication Data

US 2014/0212110 A1    Jul. 31, 2014

(30) Foreign Application Priority Data

Jan. 29, 2013   (KR) ........................ 10-2013-0009610

(51) Int. Cl.
*H04N 5/93*      (2006.01)
*H04N 5/262*     (2006.01)
*G06F 19/00*     (2011.01)
*A61B 8/00*      (2006.01)

(52) U.S. Cl.
CPC ............ *H04N 5/2624* (2013.01); *G06F 19/321* (2013.01); *H04N 5/93* (2013.01); *A61B 8/56* (2013.01)

(58) Field of Classification Search
None
See application file for complete search history.

(56) References Cited

U.S. PATENT DOCUMENTS

| | | | |
|---|---|---|---|
| 2009/0024037 A1* | 1/2009 | Baba et al. | 600/454 |
| 2009/0142030 A1* | 6/2009 | Lee et al. | 386/52 |
| 2009/0252379 A1* | 10/2009 | Kondo et al. | 382/107 |
| 2010/0008558 A1* | 1/2010 | Baeumer et al. | 382/131 |
| 2010/0253854 A1* | 10/2010 | Hong et al. | 348/699 |
| 2010/0281375 A1* | 11/2010 | Pendergast et al. | 715/723 |

FOREIGN PATENT DOCUMENTS

| | | |
|---|---|---|
| JP | 2011-041593 A | 3/2011 |
| KR | 10-2008-0044393 A | 5/2008 |

OTHER PUBLICATIONS

Communication dated Feb. 18, 2014 from the Korean Intellectual Property Office in a counterpart Korean application No. 10-2013-0009610.

* cited by examiner

*Primary Examiner* — William C Vaughn, Jr.
*Assistant Examiner* — Eileen Adams
(74) *Attorney, Agent, or Firm* — Sughrue Mion, PLLC

(57) ABSTRACT

Disclosed herein is an image display apparatus including a storage unit storing a plurality of images, an input unit receiving a selection command for selecting one or more images from among the plurality of images, and a display unit displaying at least one image of the selected images in a first zone and at least one second image of the selected images in a second zone.

24 Claims, 23 Drawing Sheets

FIG. 20
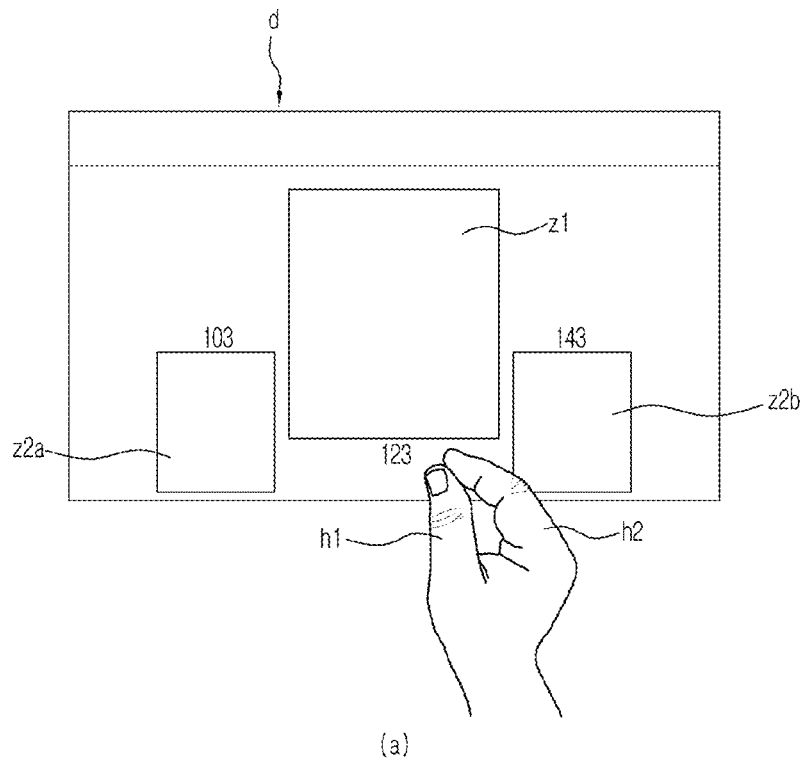
(a)
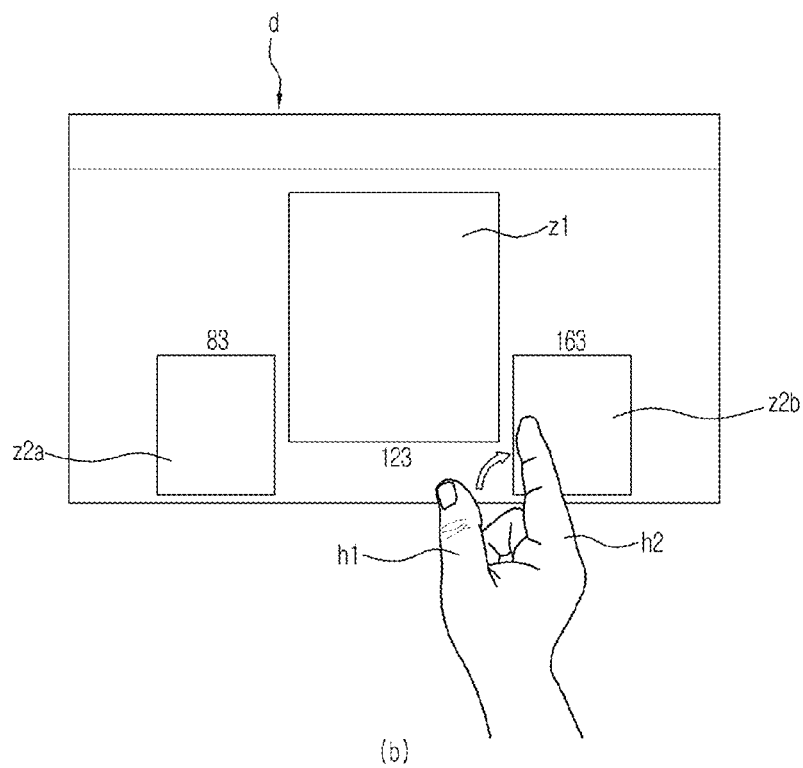
(b)

APPARATUS AND METHOD FOR DISPLAYING IMAGES

CROSS-REFERENCE TO RELATED APPLICATION

This application claims the benefit of Korean Patent Application No. 2013-0009610, filed on Jan. 29, 2013 in the Korean Intellectual Property Office, the disclosure of which is incorporated herein by reference.

BACKGROUND

1. Field

Embodiments of the present invention relate to an image display apparatus and a method for displaying images on the image display apparatus.

2. Description of the Related Art

In general, imaging apparatuses are used to photograph the external appearances, internal tissues, or structures of target subjects and/or display the photographed images. In general, an imaging apparatus include one or both of a photographing device and a display device.

The photographing device radiates visible light, infrared light, radiation such as X-ray, ultrasonic waves or the like to a target subject to collect various data about the target subject, and then creates an image of the target subject based on the collected data. Since the collected data cannot be visually interpreted or recognized as it is by a user, the photographing device performs image processing on the collected data using an image processor to acquire an image of the target subject which can be visibly recognized by a user.

The display device displays the image created by the photographing unit. Specifically, the display device displays the image, for example, a picture or an ultrasonic image in real time or in non-real time through a camera display mounted on a camera or a monitor connected to an ultrasonic imaging apparatus or the like so that the user can see the external appearance or internal tissue of the target subject.

The imaging apparatus may be a camera, a camcorder, an ultrasonic imaging apparatus, digital radiography (DR), computed tomography (CT), or a magnetic resonance imaging (MRI) apparatus. The above information disclosed in this Background section is only for enhancement of understanding of the background of the invention and therefore it may contain information that does not form any part of the prior art.

SUMMARY

Exemplary embodiments of the present invention provide a method and apparatus for simultaneously displaying a plurality of independent images acquired by an imaging apparatus or the like.

Additional aspects of the invention will be set forth in part in the description which follows and, in part, will be apparent from the description, or may be learned by practice of the invention.

In accordance with one aspect of the present invention, an ultrasonic imaging apparatus includes: a display unit; and a controller controlling the display unit to display at least one first image of a plurality of images to be displayed in a zone on a screen of the display unit, and at least one second image of the plurality of images to be displayed in the other zone on the screen of the display unit.

The second image may be an image decided according to the first image, or the first image may be an image decided according to the second image.

The ultrasonic imaging apparatus may further include an input unit receiving a selection command for selecting the first image or the second image from the outside.

In this case, the input unit may receive a selection command for selecting the first image or the second image from among the plurality of images. Also, the input unit may receive a selection command for selecting the at least one second image from the at least one first image, or a selection command for selecting the at least one first image from the at least one second image.

Meanwhile, the at least one first image may be at least one of the at least one second image, or the at least one second image may be at least one of the at least one first image.

Also, the plurality of images may be a plurality of image frames classified into at least one image group, the first image may be a first image frame, and the second image may be a second image frame. In this case, the first image frame and the second image frame may be different image frames belonging to the same image group. The second image frame may be a preceding image frame preceding the first image frame or a following image frame following the first image frame. A predetermined number of preceding image frames or a predetermined number of following image frames may be displayed in the other zone on the screen of the display unit. Also, the second image frame may be an image frame being within a predetermined frame interval from the first image frame.

Meanwhile, the first image frame and the second image frame may be image frames belonging to different image groups.

If the first image frame moves, the second image frame may move in correspondence to the movement of the first image frame, or if the second image frame moves, the first image frame may move in correspondence to the movement of the second image frame.

The display unit may be a touch screen receiving an external command according to a user's touch operation. In this case, at least one of the first image and the second image may be decided according to a user's gesture input to the touch screen.

At least one of a first image and a second image, displayed in a zone on the touch screen or in the other zone on the touch screen, may change according to a user's gesture input to the touch screen. Also, at least one of a first image and a second image, displayed in a zone on the touch screen or in the other zone on the touch screen, may be fixed according to a user's gesture input to the touch screen.

Meanwhile, when the first image changes according to a touch operation input to the touch screen, the second image may change in correspondence to the change of the first image, or when the second image changes according to a touch operation input to the touch screen, the first image may change in correspondence to the change of the second image.

Also, the plurality of images may be a plurality of image frames classified into at least one image group, the first image may be a first image frame, the second image may be a second image frame, and a frame interval between the first image frame and the second image frame may be decided according to a touch operation input to the touch screen.

In accordance with an exemplary embodiment of the invention, an ultrasonic imaging apparatus may include a controller controlling the display unit to display: a first set of images comprising at least one first image of a plurality of images to be displayed in a first zone of a screen of the display unit, and a second set of images comprising at least one second image of the plurality of images to be displayed in a second zone of the screen of the display unit. The first image may be an image of the second set of images, or the second image may be an image of the first set of images.

The first image frame and the second image frame may be included in a ordered sequence of frames. The second image frame may be preceding the first image frame in the sequence of frames or the second image frame may be following the first image frame in the sequence of frames.

If the first zone displays a first video as a sequence of frames comprising the first image frame, then the second zone may display a second video as a sequence of frames comprising the second image frame and the second video is displayed in relation to the first video. If the second zone displays a second video as a sequence of frames comprising the second image frame, then the first zone may display a first video as a sequence of frames comprising the first image frame and the first video is displayed in relation to the second video.

In accordance with another aspect of the present invention, an X-ray imaging apparatus includes: a display unit; and a controller controlling the display unit to display at least one first image of a plurality of images to be displayed in a zone on a screen of the display unit, and at least one second image of the plurality of images to be displayed in the other zone on the screen of the display unit.

In accordance with another aspect of the present invention, an ultrasonic image display method includes: acquiring a plurality of images; deciding at least one first image and at least one second image from the plurality of images; and displaying the at least one first image in a first zone of a display screen, and the at least one second image in a second zone of the display screen.

The deciding of the first image and the second image may include: selecting the at least one first image from among the plurality of images; and deciding the at least one second image based on the at least one first image selected from among the plurality of images. In this case, the at least one second image may be different from the at least one first image.

The second image may be a preceding image preceding the first image or a following image following the first image. The second image mat be a preceding image preceding the first image or a following image following the first image in a sequence of frames comprising the first image and the second image.

Also, the deciding of the first image and the second image may include selecting the at least one first image and the at least one second image that is different from the first image, from among the plurality of images.

The deciding of the first image and the second image may include: deciding a plurality of second images from the plurality of images; displaying the decided second images in a second zone of the display screen; and selecting at least one first image from among the second images displayed in the second zone of the display screen.

In accordance with another aspect of the present invention, an X-ray image display method includes: acquiring a plurality of images; deciding at least one first image and at least one second image from the plurality of images; and displaying the at least one first image in a first zone of a display screen, and the at least one second image in a second zone of the display screen.

According to the image display apparatus and method as described above, it is possible to simultaneously display a plurality of images on a screen.

Also, a user can easily search for images that he/she wants to see.

Furthermore, the user can see an image taken at a specific time together with another image taken within a predetermined time period from the specific time to compare the images.

More specifically, when the image display apparatus is a radiation imaging apparatus, such as digital radiography (DR) or computed tomography (CT), or an ultrasonic imaging apparatus, the user can selectively display a plurality of ultrasonic images or a plurality of radiation images, and compare and analyze the images, thereby more accurately understanding the internal tissue or structure of a target subject, which will lead to an accurate determination of lesion and the like and help diagnose patients. It is to be understood that both the foregoing general description and the following detailed description are exemplary and explanatory and are intended to provide further explanation of the invention as claimed.

BRIEF DESCRIPTION OF THE DRAWINGS

These and/or other aspects of the invention will become apparent and more readily appreciated from the following description of the embodiments, taken in conjunction with the accompanying drawings of which:

FIGS. 17 to 20 are views for describing various touch inputs for an ultrasonic imaging apparatus having a touch screen, according to exemplary embodiments of the present invention.

DETAILED DESCRIPTION

Figure 1:
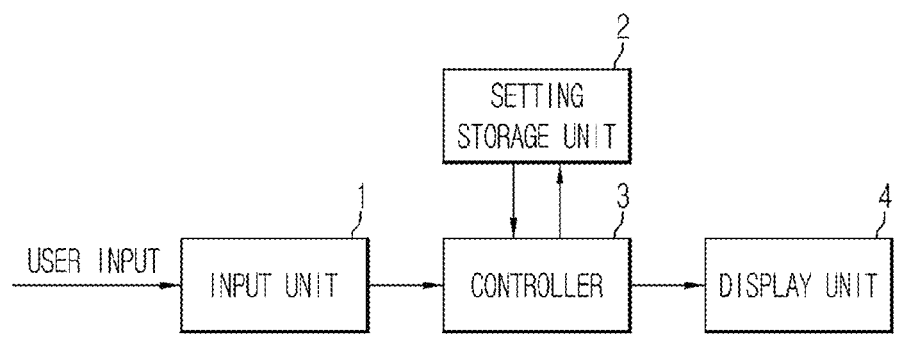
FIG. 1 is a block diagram of an image display apparatus according to an exemplary embodiment of the present invention.

Reference will now be made in detail to the embodiments of the present invention, examples of which are illustrated in the accompanying drawings, wherein like reference numerals refer to like elements throughout. This invention may, however, be embodied in many different forms and should not be construed as limited to the embodiments set forth herein. Rather, these embodiments are provided so that this disclosure is thorough, and will fully convey the scope of the invention to those skilled in the art. In the drawings, the size and relative sizes of layers and regions may be exaggerated for clarity. Like reference numerals in the drawings denote like elements.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

Throughout the drawings and the detailed description, unless otherwise described, the same drawing reference numerals are understood to refer to the same elements, features, and structures. The relative size and depiction of these elements may be exaggerated for clarity.

Although some features may be described with respect to individual exemplary embodiments, aspects need not be limited thereto such that features from one or more exemplary embodiments may be combinable with other features from one or more exemplary embodiments.

The aspects of the invention in this application are not limited to the disclosed operations and sequence of operations. For instance, operations may be performed by various elements and components, may be consolidated, may be omitted, and may be altered without departing from the spirit and scope of the present invention.

(1) Hereinafter, an image display apparatus according to an embodiment of the present invention will be described with reference to FIGS. 1 to 4. FIG. 1 is a block diagram of an image display apparatus according to an exemplary embodiment of the present invention. Referring to FIG. 1, the image display apparatus may include an input unit 1, a setting storage unit 2, a controller 3, and a display unit 4.

The input unit 1 receives various instructions or commands, such as a start command, a display mode selection command, a display command, and an image movement command, from a user.

The setting storage unit 2 stores various setting information that is used by the controller 3 to control the display unit 4. The various setting information includes formats of images that are to be displayed on the display unit 4, locations at which the images are to be displayed, the number of the images (e.g., the number of first images, the number of second images, or sizes of the images), a relationship between the images (e.g., a relationship between the first and second images), information about zones in which the images are to be displayed, etc.

The controller 3 controls the display unit 4 according to a user' command received through the input unit 1 or according to various setting information stored in the setting storage unit 2.

The display unit 4 displays a plurality of images on a screen according to a control command from the controller 3.

Figure 2:
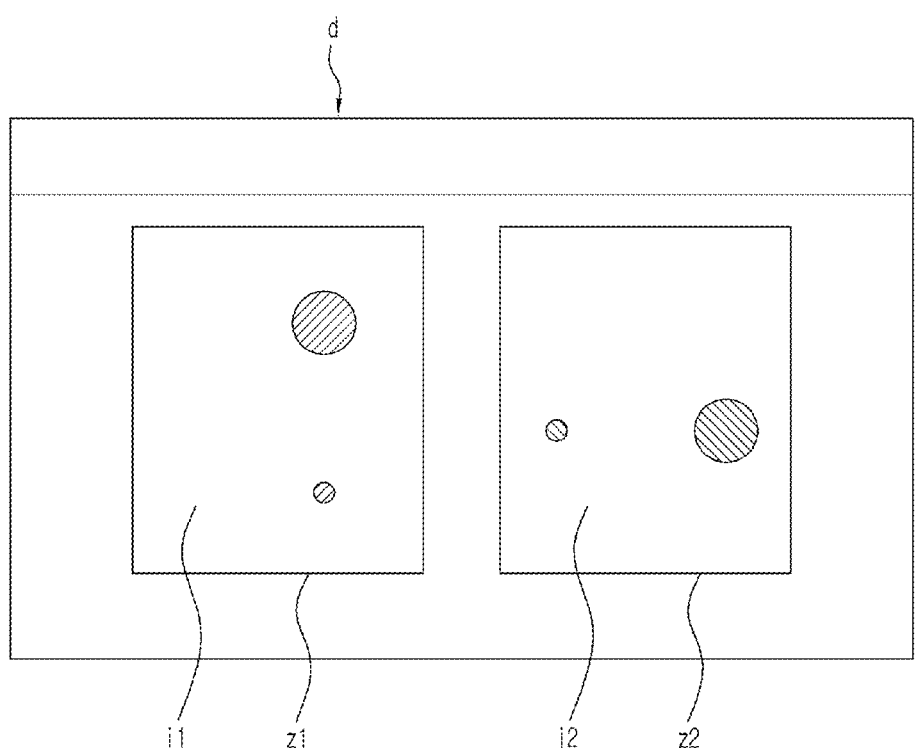
FIGS. 2 and 3 illustrate images displayed on a display unit, according to exemplary embodiments of the present invention.

FIG. 2 illustrates images displayed on the display unit 4, according to an exemplary embodiment of the present invention. As illustrated in FIG. 2, the display unit 4 may display a plurality of images, for example, first and second images i1 and i2 on a screen d. More specifically, the display unit 4 may display the first image i1 in an area of the screen d, and the second image i2 in another area of the screen d.

In order for the display unit 4 to display the first image i1 in an area of the screen d, and the second image i2 in another area of the screen d, the screen d of the display unit 4 is divided into a plurality of zones capable of displaying different images. Each zone corresponds to an area of a screen that is displayed on the display unit 4. The screen d may be divided into two zones, as illustrated in FIG. 2, or into three zones or more.

In the example of FIG. 2, one of the divided zones is referred to as a first zone z1, and the other one of the zones is referred to as a second zone z2. According to one exemplary embodiment, as illustrated in FIG. 2, the first and second zones z1 and z2 are displayed not to overlap each other. According to another exemplary embodiment, the first and second zones z1 and z2 overlap partially. The first and second zones z1 and z2 may have the same size, that is, the same width and height. However, the first and second zones z1 and z2 may have different sizes. That is, the first and second zones z1 and z2 may have different widths and/or heights. In this case, the first and second zones z1 and z2 may have the same ratio of height to width although the width and height of the first zone z1 are different from those of the second zone z2.

The first image i1 is displayed on the first zone z1 that is an area of the screen d, and the second image i2 is displayed on the second zone z2 that is another area of the screen d. If the size of the first zone z1 is different from that of the second zone z2, the first and second images i1 and i2 may also be displayed with different sizes.

Also, the first image i1 displayed in the first zone z1 and the second image i2 displayed in the second zone z2 may be the same image or different images.

Also, a plurality of first images i1 may be displayed in the first zone z1 simultaneously or at different times. Likewise, a plurality of second images i2 may be displayed in the second zone z2 simultaneously or at different times.

The first image i1 and/or the second image i2 may be a moving image. In this case, the first and second images i1 and i2 may be played back at the same playback speed or at different playback speeds, simultaneously or at different times. Alternatively, the first image i1 may be first played back, and then, the second image i2 may be played back in response to the playback of the first image i1.

Also, one of the first and second images i1 and i2 may be played back, and the remaining one may be displayed as a still image.

The first image i1 may be at least one of a plurality of images belonging to a predetermined image group. The predetermined image group is a group of a plurality of images. For example, a group of a plurality of images is a group of a plurality of image frames forming a moving image. Like the first image i1, the second image i2 may be at least one of a plurality of images belonging to a predetermined image group.

In this case, the first and second images i1 and i2 may belong to the same image group or to different image groups. That is, the first and second images i1 and i2 may be selected from the same image group or from different image groups.

Figure 3:
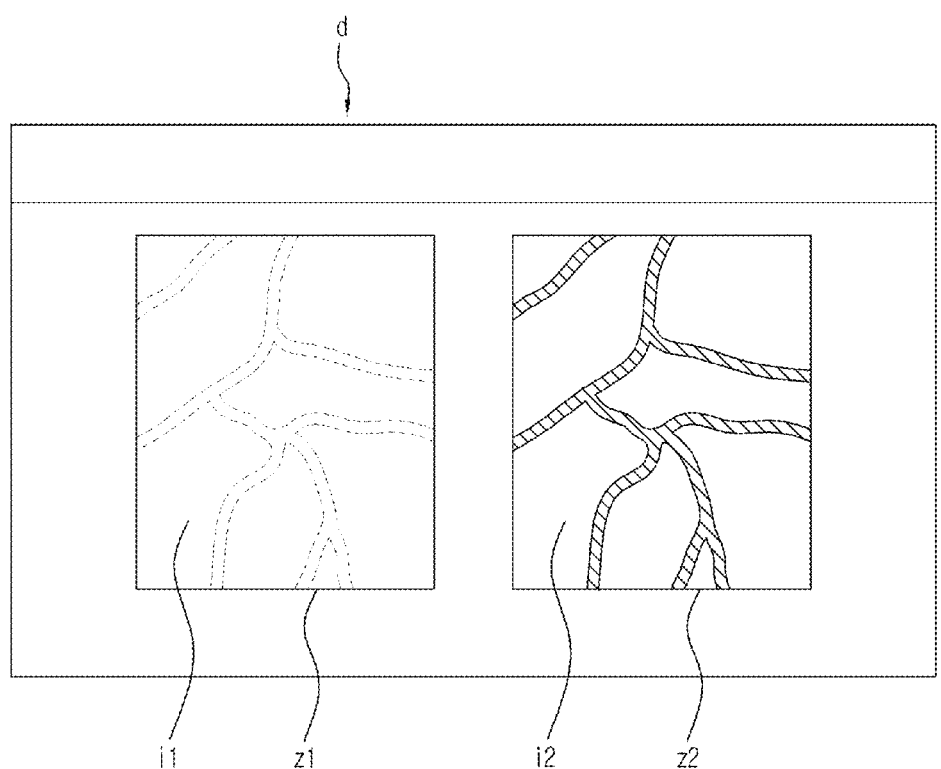

An example in which the first and second images i1 and i2 belong to different image groups will be described with reference to FIG. 3, as follows. FIG. 3 illustrates images displayed on a display unit of an ultrasonic imaging apparatus, according to an embodiment of the present invention.

An ultrasonic imaging apparatus may scan a target area several times. For example, the ultrasonic imaging apparatus scans a target area (e.g., blood vessels) without injecting contrast media, then injects contrast media, and again scans the target area. As a result, the ultrasonic imaging apparatus can acquire a group of ultrasonic images for the target area when no contrast media is injected by the first scanning, and acquire another group of ultrasonic images for the target area after contrast media is injected by the second scanning.

Then, the ultrasonic imaging apparatus displays the group of ultrasonic images (referred as first images i1) acquired by the first scanning in a first zone z1 of a screen d, and displays the other group of ultrasonic images (referred as second images i2) acquired by the second scanning in a second zone z2 of the screen d. In this way, the ultrasonic imaging apparatus can simultaneously display images taken before contrast media is injected together with images taken after contrast media is injected, on the same screen. Thus, an operator may easily compare the images taken before contrast media has been injected with the images taken after contrast media has been injected.

A screen on which the first images i2 taken by the first scanning and the second images i2 taken by the second scanning are displayed together is illustrated in FIG. 3. As illustrated in FIG. 3, the first zone z1 located to the left of the screen d displays the first images i1 for the target area before contrast media is injected, and the second zone z2 located to the right of the screen d displays the second images i2 for the target area after contrast media is injected. Accordingly, a user can compare ultrasonic images taken before contrast media is injected to ultrasonic images taken after contrast media is injected.

Figure 4:
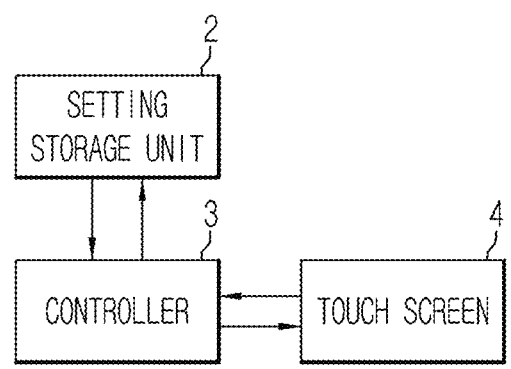
FIG. 4 is a block diagram of an image display apparatus according to another exemplary embodiment of the present invention.

FIG. 4 is a block diagram of an image display apparatus according to another exemplary embodiment of the present invention. Referring to FIG. 4, the image display apparatus may include a setting storage unit 2, a controller 3, and a touch screen 4.

The touch screen 4 has all functions of the input unit 1 and the display unit 4 described above with reference to FIG. 1. The touch screen 4 senses a touch input (e.g., a single-touch input or a multi-touch input) from a user, thus receiving a predetermined command (e.g., selections of images, playing back moving images, etc.) from the user. The touch screen 4 may display a plurality of images. Referring to FIGS. 2 and 3, a screen of the touch screen 4 may also be divided into a plurality of zones z1 and z2. The respective zones z1 and z2 may display predetermined images i1 and i2. However, the individual zones z1 and z2 of the touch screen 4 may receive commands for the displayed images i1 and i2, as well as displaying the images i1 and i2. Accordingly, a user can intuitively input commands (e.g., a playback command, a selection command, a change command, etc.) for the images i1 and i2 to the touch screen 4, while seeing the images i1 and i2.

Figure 5:
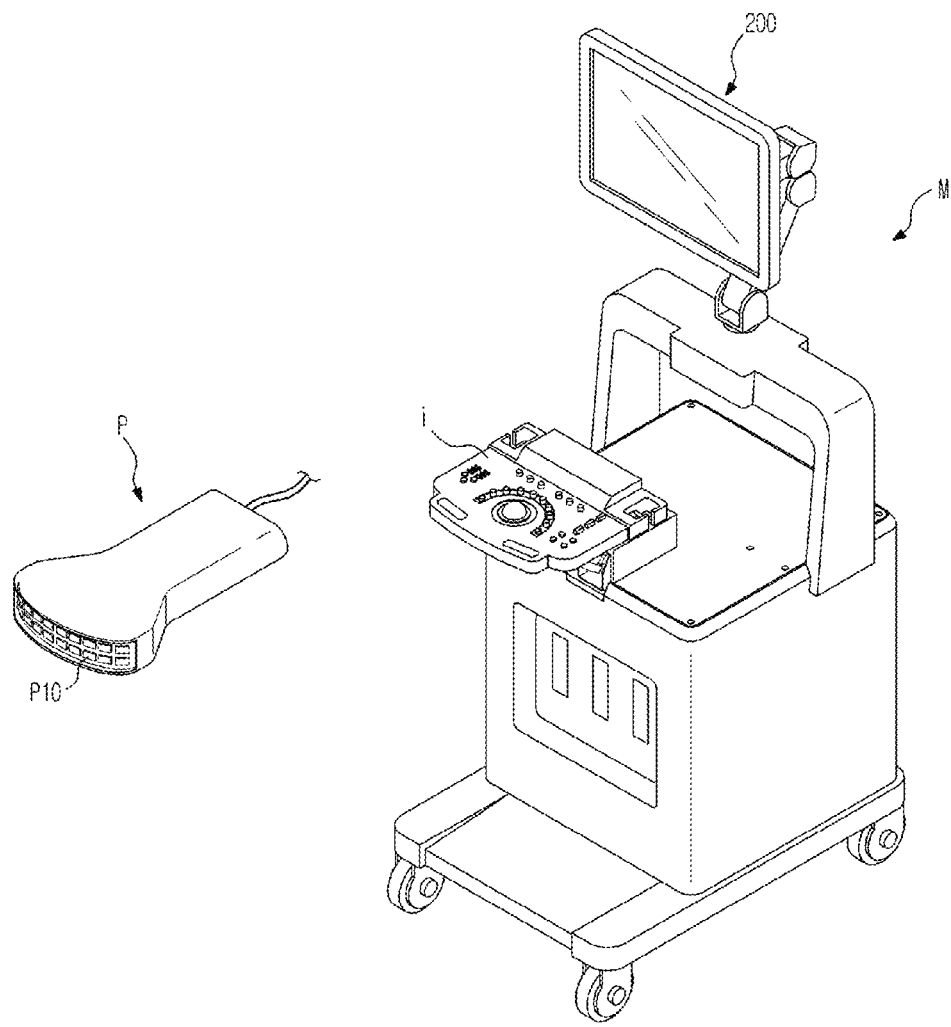
FIG. 5 is a perspective view of an ultrasonic imaging apparatus according to an exemplary embodiment of the present invention.
Figure 6:
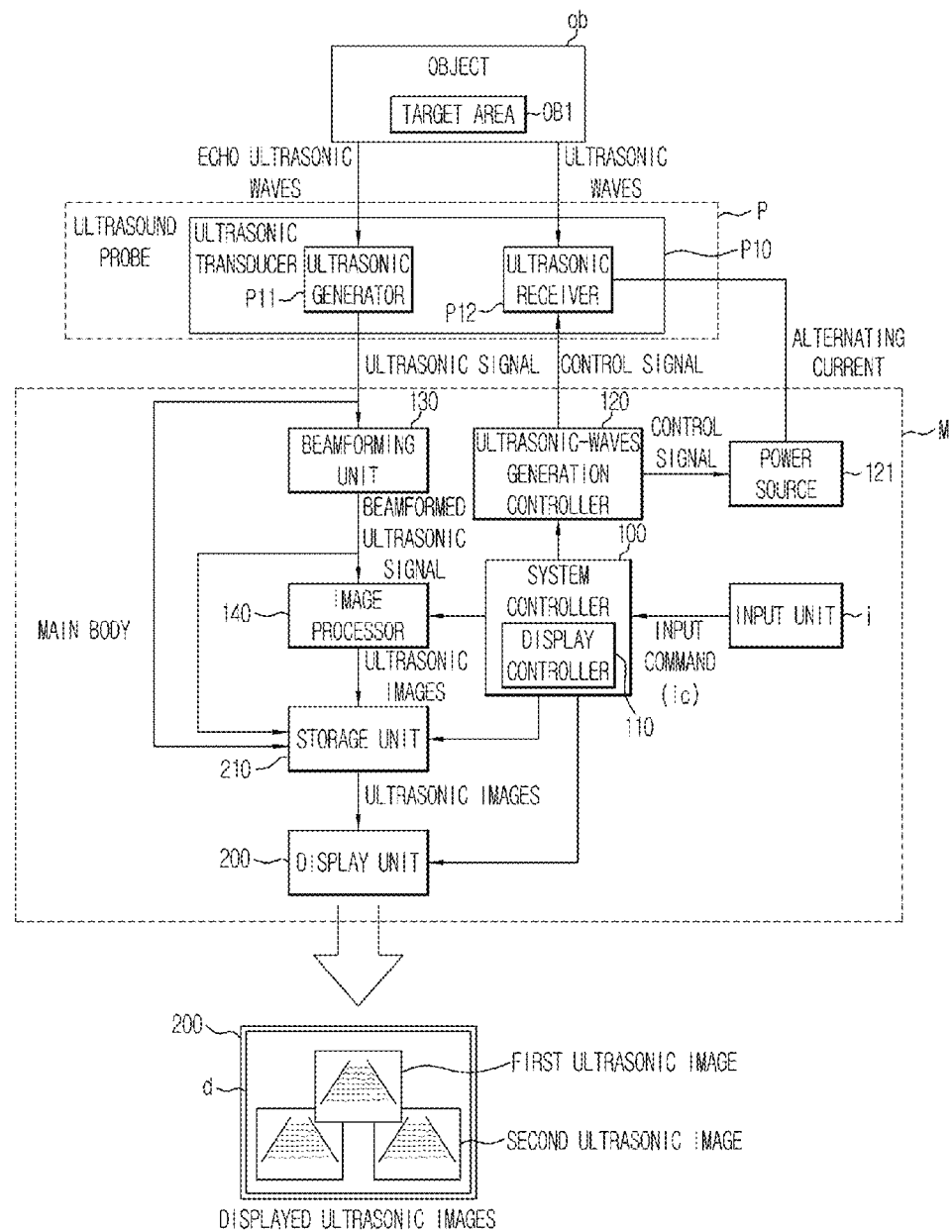
FIG. 6 is a block diagram of an ultrasonic imaging apparatus according to an exemplary embodiment of the present invention.

(2) Hereinafter, an ultrasonic imaging apparatus according to exemplary embodiments of the present invention will be described with reference to FIGS. 5 to 19. FIG. 5 is a perspective view of an ultrasonic imaging apparatus according to an exemplary embodiment of the present invention, and FIG. 6 is a block diagram of the ultrasonic imaging apparatus according to an exemplary embodiment of the present invention. As illustrated in FIGS. 5 and 6, the ultrasonic imaging apparatus includes an ultrasound probe P for collecting ultrasonic image data from an object ob, and a main body M for controlling the ultrasound probe P and creating ultrasonic images using the collected ultrasonic image data.

The ultrasound probe P may include an ultrasonic generator P11 for generating ultrasonic waves, and an ultrasonic receiver P12 for receiving ultrasonic waves reflected from a target area ob1 or generated in the target area ob1. The ultrasound probe P generates ultrasonic waves according to supplied power, radiates the ultrasonic waves to the target area ob1 of the object ob, receives echo ultrasonic waves reflected from the target area ob1, and then converts the echo ultrasonic waves into electrical signals.

For example, if an alternating current is applied to the ultrasonic generator P11 of the ultrasound probe P under the control of an ultrasonic-waves generation controller 120 installed in the ultrasound probe P or in an external apparatus such as the main body M, the ultrasonic generator P11 vibrates according to the alternating current to generate ultrasonic waves. The ultrasonic waves generated by the ultrasonic generator P11 are radiated to the object ob, and then reflected from the target area ob1 of the object ob.

The ultrasonic receiver P12 receives echo ultrasonic waves reflected from the target area ob1, vibrates according to the frequency of the echo ultrasonic waves to convert the echo ultrasonic waves into a predetermined electrical signal, and outputs the predetermined electrical signal as an ultrasonic signal.

When the ultrasonic imaging apparatus is a combination of an ultrasonic imaging apparatus and a photoacoustic imaging apparatus, the ultrasonic receiver P12 may receive sound waves (for example, ultrasonic waves) generated from the target area ob1 after a laser irradiator of the photoacoustic imaging apparatus radiates laser beams.

According to one exemplary embodiment of the ultrasound probe P, the ultrasonic generator P11 and the ultrasonic receiver P12 are implemented as an ultrasonic transducer P10 installed in one end of the ultrasound probe P. A transducer is a device for converting a specific type of energy (for example, electrical energy) into another type of energy (for example, wave energy or light energy). The ultrasonic transducer P10 converts wave energy of ultrasonic waves into electrical energy and vice versa. In detail, the ultrasonic transducer P10 enables a piezoelectric vibrator or a thin film to vibrate according to an alternating current supplied from a power source 121, such as an external power supply or an internal energy storage (e.g., a battery) and to generate ultrasonic waves. Also, when the ultrasonic transducer P10 receives ultrasonic waves (e.g., echo ultrasonic waves) from the outside, the piezoelectric vibrator or the thin film vibrates according to the frequency of the echo ultrasonic waves, and the ultrasonic transducer P10 generates an alternating current having a frequency corresponding to the vibration frequency, and outputs the alternating current to the outside. In this way, the ultrasonic transducer P10 converts ultrasonic waves into an ultrasonic signal. That is, the ultrasonic transducer P10 can perform all functions of the ultrasonic generator P11 and the ultrasonic receiver P12.

The ultrasonic transducer P10 may be a Magnetostrictive Ultrasonic Transducer (MUT) using a magnetostrictive effect of magnetic materials, a Piezoelectric Ultrasonic Transducer (PUT) using a piezoelectric effect of piezoelectric materials, or a Capacitive Micromachined Ultrasonic Transducer (CMUT) transmitting/receiving ultrasonic waves using vibrations of several hundreds or thousands of micromachined thin films. In addition, the ultrasonic transducer P10 may be any type of transducer capable of generating ultrasonic waves according to an electrical signal or generating an electrical signal according to ultrasonic waves.

Referring to FIG. 6, the ultrasonic generator P11 of the ultrasonic transducer P10 generates a plurality of channels of ultrasonic signals, and transfers the generated ultrasonic signals to a beamingforming unit 130 of the main body M.

The main body M may include a system controller 100, the ultrasonic-waves generation controller 120, the beamforming unit 130, an image processor 140, a display unit 200, and a storage unit 210.

The system controller 100 controls the entire operations of the main body M or of the main body M and the ultrasound probe P. According to one exemplary embodiment, the system controller 100 may further include a display controller 100 for controlling the display screen of the display unit 200.

The system controller 100 analyzes a user's instruction or command received through an input unit i, and generates an appropriate control command according to the user's instruction or command.

The input unit i receives predetermined instructions or commands from a user for controlling the ultrasonic imaging apparatus. The input unit i may be mounted on the main body M, as illustrated in FIG. 5. Alternatively, the input unit i may be separated from the main body M, and in this case, the input unit i may transmit received user's instructions or commands to the main body M through a wired/wireless communication network.

More specifically, the input unit i may receive a command for selecting a first image, a second image, or both the first and second images, which will be described later. Also, the input unit i may receive commands for selecting more images, such as a third image, a fourth image, etc.

The input unit i may include various user interfaces (UIs), such as a keyboard, a mouse, a trackball, a touch screen, and a paddle. Also, the input unit i may be a separate work station connected to the main body M directly or through a wired/wireless communication network.

The ultrasonic-waves generation controller 120 of the main body M receives a control command from the system controller 100, generates a predetermined control signal according to the received control command, and transfers the predetermined control signal to the ultrasonic generator P11. Then, the ultrasonic generator P11 vibrates according to the control signal to generate ultrasonic waves.

Also, the ultrasonic-waves generation controller 120 may generate a separate control signal for controlling the power source 121 electrically connected to the ultrasonic generator P11, and transfer the control signal to the power source 121. The power source 121 applies a predetermined alternating current to the ultrasonic generator P11 according to the received control signal. Then, the ultrasonic generator P11 vibrates according to the alternating current to generate ultrasonic waves, and radiates the ultrasonic waves to the target area ob1 of the object ob.

Figure 7:
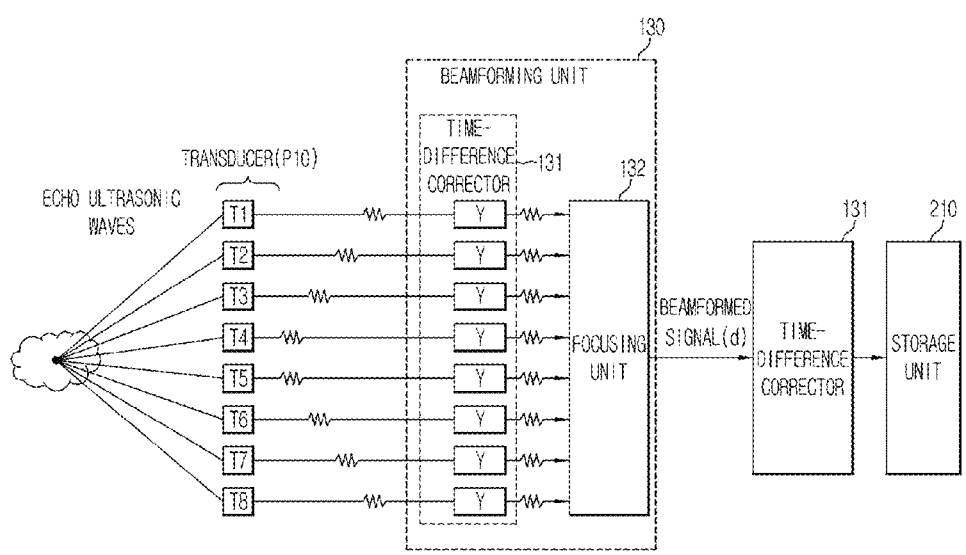
FIG. 7 is a view for describing beamforming of an ultrasonic imaging apparatus, according to an exemplary embodiment of the present invention.

The beamforming unit 130 of the main body M receives the ultrasonic signal transferred from the ultrasonic receiver P12, and performs beamforming on the received ultrasonic signal. FIG. 7 illustrates the beamforming unit 130 of the ultrasonic imaging apparatus, according to an exemplary embodiment of the present invention. Referring to FIG. 7, the beamforming unit 130 includes a parallax corrector 131 and a focusing unit 132.

The time-difference corrector 131 corrects time differences between ultrasonic signals generated by individual ultrasonic transducers T1 through T8. Ultrasonic waves reflected from the target area ob1 of the object ob or induced by laser or the like are received by the ultrasonic receiver P11, for example, the ultrasonic transducer P10. However, since distances of the ultrasonic transducers T1 through T8 to the target area ob1 are different and ultrasonic waves are transmitted at the nearly same speed, ultrasonic waves reflected/generated from the same target area ob1 will be received at different times by the ultrasonic transducers T1 through T8. In other words, the ultrasonic transducers T1 through T8 receive ultrasonic signals with time differences. The time-difference corrector 131 corrects these time differences between ultrasonic signals. For example, the time-difference corrector 131 may delay transmission of an ultrasonic signal (s) of a specific channel(s) by a predetermined time period(s) so that ultrasonic signals of all channels can be transferred at the same time to the focusing unit 132.

The focusing unit 132 focuses the ultrasonic signals whose time differences have been corrected. Specifically, the focusing unit 132 gives predetermined weights, that is, predetermined beamforming coefficients to ultrasonic signals of respective channels to enhance or relatively attenuate ultrasonic signals of specific channels, thereby focusing the ultrasonic signals. In this way, the focusing unit 132 can create ultrasonic images that meet a user's requirements or convenience. According to one exemplary embodiment, the focusing unit 132 may focus ultrasonic signals received by the ultrasonic receiver P12 using predetermined beamforming coefficients regardless of the ultrasonic signals (data-independent beamforming), or focus the received ultrasonic signals using optimal beamforming coefficients calculated based on the ultrasonic signals (data-dependent beamforming or adaptive beamforming).

The ultrasonic signals beamformed by the beamforming unit 130 are transferred to the image processor 140. According to another exemplary embodiment, the beamformed ultrasonic signals may be directly transferred to the storage unit 210.

The image processor 140 creates and restores an ultrasonic image based on the beamformed ultrasonic signals. More specifically, the image processor 140 may restore an ultrasonic image from the beamformed ultrasonic signals to be nearly the same as or similar to the original image, using various transformation functions such as a point spread function (psf).

Figure 8:
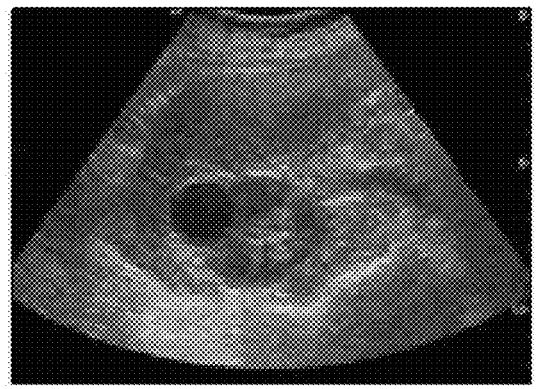
FIG. 8 illustrates an ultrasonic image created by an ultrasonic imaging apparatus, according to an exemplary embodiment of the present invention.

The image processor 140 may create ultrasonic images in several modes, such as an A mode and a B mode, based on the beamformed ultrasonic signals. The mode A is for representing ultrasonic images using amplitudes. Specifically, the A mode is for representing strengths of reflection as amplitudes based on a distance or an ultrasonic-waves transmission time between the ultrasound probe P and the target area ob1. The B mode is to represent magnitudes of echo ultrasonic waves as brightness values on a screen. FIG. 8 illustrates an example of an ultrasonic image created in the B mode by the ultrasonic imaging apparatus. When a user sees an ultrasonic image created in the B mode, the user can intuitively recognize and understand the internal tissue or structure of an object included in the ultrasonic image, and accordingly, the B mode is widely used in various industrial fields.

Also, the image processor 140 may correct the restored ultrasonic image according to a user's intention or for a user's convenience. For example, the image processor 140 may correct the brightness, luminance, contrast, and/or colors of the entire or a part of an ultrasonic image so that a user can clearly see tissues in the ultrasonic image.

Figure 9:
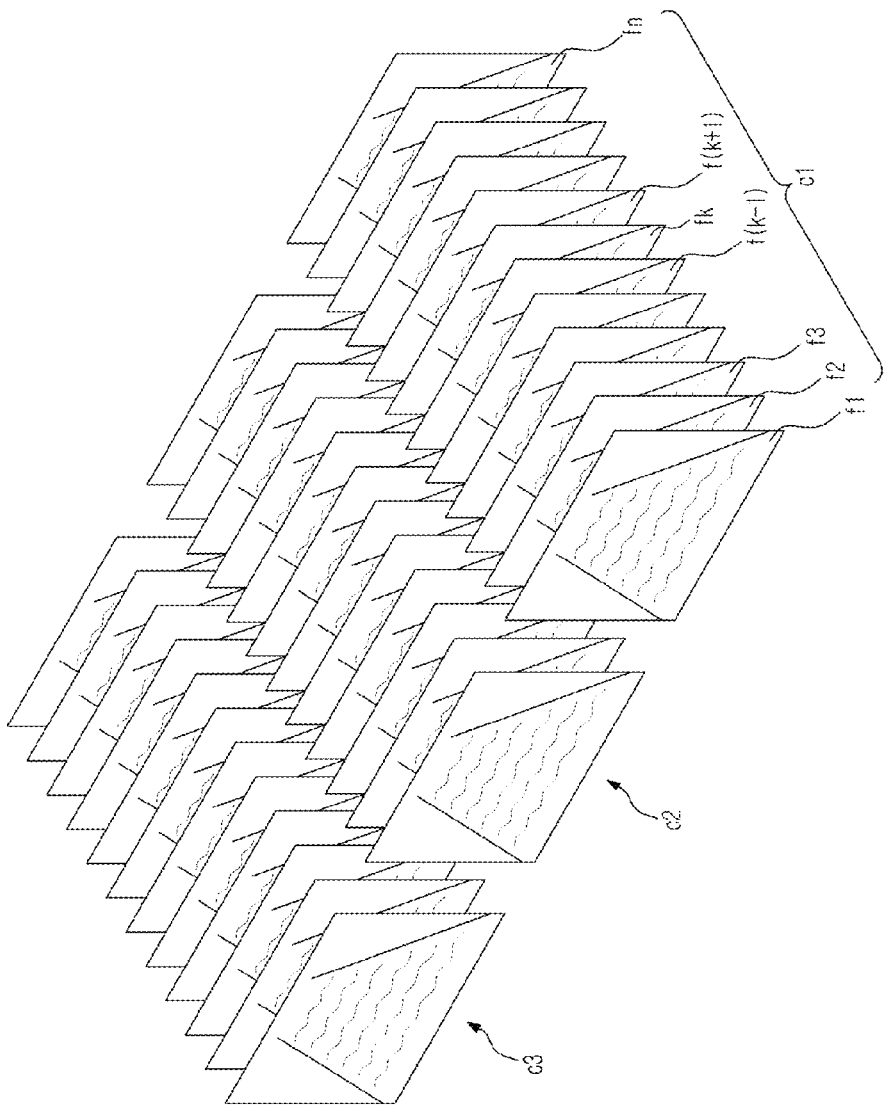
FIG. 9 illustrates a plurality of ultrasonic images created by an ultrasonic imaging apparatus.

The image processor 140 may restore a plurality of ultrasonic images. FIG. 9 illustrates a plurality of ultrasonic images created by the ultrasonic imaging apparatus. For example, the ultrasound probe P of the ultrasonic imaging apparatus radiates ultrasonic waves to a target area ob1 of an object ob several times, and collects a plurality of ultrasonic signals for the target area ob1. Then, the beamforming unit 130 performs beamforming on the individual ultrasonic signals, and the image processor 140 restores a plurality of ultrasonic images f1 through fn as illustrated in FIG. 9 based on the beamformed ultrasonic signals.

Specifically, the ultrasonic imaging apparatus may radiate ultrasonic waves at regular time intervals, for example, based on frames per second (fps), and thus create a plurality of successive ultrasonic images f1 through fn at regular time intervals. When the plurality of successive ultrasonic images f1 through fn are sequentially displayed on a screen, a user can see a moving image, that is, an ultrasound video.

The plurality of ultrasonic images f1 through fn may be classified into a predetermined number of image groups; first, second and third image groups c1, c2, and c3. The image groups are groups of a plurality of ultrasonic images, classified according to predetermined classification criteria, for example, according to imaging/photographing conditions or imaging/photographing times. With regard to the example of FIG. 3, the first image group c1 may be a group of ultrasonic images for blood vessels taken before contrast media is injected, and a second image group c2 may be a group of ultrasonic images for the blood vessels taken after contrast media is injected.

A plurality of ultrasonic images included in the first image group c1 may be a plurality of ultrasonic image frames forming an ultrasonic moving image. Accordingly, when a plurality of ultrasonic images belonging to the same group are displayed on a screen in order of time or in reverse order of time, a moving image may be displayed.

The storage unit 210 may temporarily or permanently store beamformed ultrasonic signals (RF signals) output from the beamforming unit 130 or ultrasonic image signals for images generated or corrected by the image processor 140. The storage unit 210 may store the ultrasonic images in the form of row data, or in the form of processed data subject to predetermined image processing, for example, in the form of a file of a plurality of graphic images.

The display unit 200 may display beamformed ultrasonic signals output from the beamforming unit 130, ultrasonic image signals subject to predetermined image processing by the image processor 140, or beamformed ultrasonic signals or image-processed ultrasonic image signals stored in the storage unit 210 on a screen.

Figure 10:
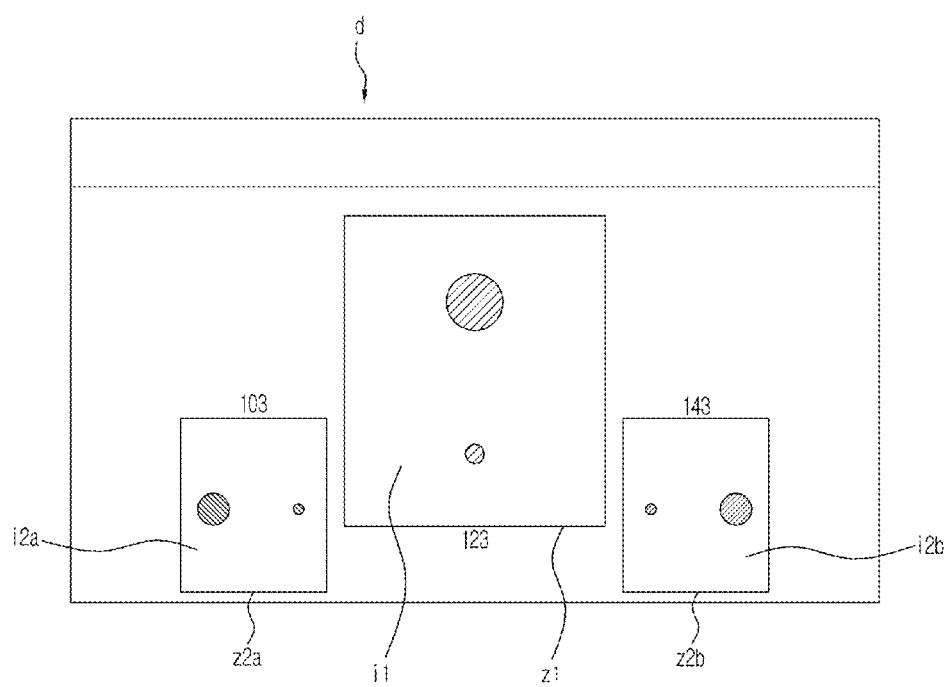
FIG. 10 illustrates a screen displayed on a display unit of an ultrasonic imaging apparatus, according to an exemplary embodiment of the present invention.

FIG. 10 illustrates a screen displayed on the display unit 200 of the ultrasonic imaging apparatus, according to an exemplary embodiment of the present invention. Referring to FIG. 10, the display unit 200 displays a plurality of ultrasonic images i1, i2a, and i2b on a screen d. In order to display a plurality of images on a screen, the screen d may be divided into a plurality of zones z1, z2a, and z2b. Each of the zones z1, z2a, and z2b displays at least one ultrasonic image.

The zones z1, z2a, and z2b may have fixed sizes defined by predetermined widths and heights. Alternatively, the sizes of the zones z1, z2a, and z2b may vary according to the sizes or resolutions of the ultrasonic images i1, i2a, and i2b or according to a user's command for changing the sizes of the zones z1, z2a, and z2b. Also, the locations of the zones z1 through z2b may be fixed according to a predetermined setting or may vary according to the sizes of the ultrasonic images i1, i2a, and i2b or according to a user's selection. The screen d may also be divided into a predetermined, fixed number of zones. Referring to the example of FIG. 10, a screen d is divided into three zones z1, z2a, and z2b. However, a screen may be divided into four zones or more. Alternatively, the screen d may be divided into a different number of zones according to the sizes of the individual zones z1, z2a, and z2b, the sizes of the ultrasonic images i1, i2a, and i2b, a user's selection, etc. The locations, sizes, and number of these zones z1, z2a, and z2b may be decided according to predetermined settings or according to a user's selection command received through the input unit 1 (see FIG. 1).

The zones z1, z2a, and z2b may display the same ultrasonic image or different ultrasonic images. Each of ultrasonic images displayed on the zones z1, z2a, and z2b may be one of a plurality of ultrasonic images belonging to at least one image group as illustrated in FIG. 9. In this case, ultrasonic images displayed on the respective zones z1, z2a, and z2b may be images belonging to the same image group or images belonging to different image groups. For example, the ultrasonic image i1 displayed on the first zone z1 and the ultrasonic images i2a and i2b displayed on the second zones z2a and z2b may be images included in the first image group c1. As another example, the ultrasonic image i1 displayed on the first zone z1 may be an image included in the first image group c1, and the ultrasonic images i2a and i2b displayed on the second zones z2a and z2b may be images included in the second image group c2 which is different from the first image group c1.

In order to display a plurality of images on a screen, referring again to FIG. 6, the display unit 200 may receive a predetermined control command from the system controller 100.

Figure 11:
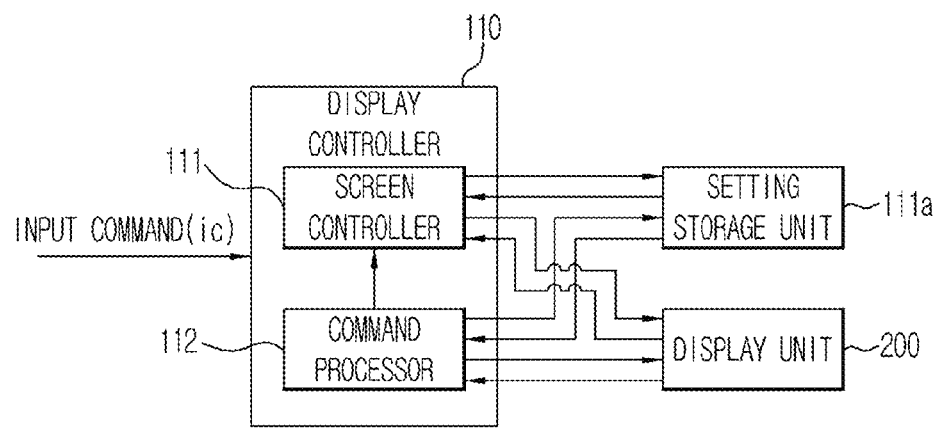
FIG. 11 is a block diagram of a display controller according to an exemplary embodiment of the present invention.

The system controller 100 may include a display controller 110 for controlling the display unit 200 to display beamformed ultrasonic signals output from the beamforming unit 130, ultrasonic image signals subject to predetermined image processing by the image processor 140, or beamformed ultrasonic signals or image-processed ultrasonic image signals stored in the storage unit 210 on a screen. FIG. 11 is a block diagram of the display controller 110 according to an exemplary embodiment of the present invention. Referring to FIG. 11, the display controller 110 may include a screen controller 111 and a command processor 112.

Referring to FIGS. 6 and 11, the screen controller 111 controls the entire screen that is displayed on the display unit 200. For example, the screen controller 111 decides the types, contents, or display locations of various information that is to be displayed on a screen of the display unit 200, the number of ultrasonic images that are to be displayed on the screen of the display unit 200, the number of zones into which the screen of the display unit 200 is divided, and/or locations or zones (for example, first and second zones) in which the respective ultrasonic images are to be displayed on the screen, thereby setting a screen layout of the display unit 200. Also, the screen controller 111 controls the display unit 200 to display a screen according to the screen layout.

According to one exemplary embodiment, the screen controller 111 reads various setting information (referring to the example of FIG. 10, the number of zones z1, z2a, and z2b into which a screen d is divided, sizes and locations of the zones z1, z2a, and z2b, images that are basically displayed on the zones z1, z2a, and z2b, information that is additionally displayed on the zones z1, z2a, and z2b, and/or a graphic interface) stored in a setting storage unit 111a, decides a screen layout of the display unit 200 according to the setting information, and controls a screen of the display unit 200 according to the screen layout.

The image processor 140 analyzes a user's instruction or command ic received through the input unit I (see FIG. 1), generates a control command corresponding to the result of the analysis, and transfers the control command to the screen controller 111 or the display unit 200. For example, when a user inputs a selection command ic for selecting an image that are to be displayed on the first zone z1, the command processor 112 analyzes the selection command ic, and transfers a control command instructing the display unit 200 to display the selected image on the first zone z1, to the display unit 200, in response to the selection command ic.

Alternatively, referring to the example of FIG. 10, when a user selects a first image i1 as an image that is to be displayed on a first zone z1, the command processor 112 may decide the second images i2 according to the first image i1, and may control the display unit 200 to display the first image i1 in a first zone z1 and the second images i2 in second zones z2.

Referring again to the example of FIG. 10, when an ultrasonic image included in the first image group c1 is selected as a first image i1, the command processor 112 may decide ultrasonic images preceding and following the first image i1, spaced by a predetermined period (or a time period selected by a user) from the first image i1 or taken within a predetermined time period (or a time period selected by a user) from the photographing time of the first image i1, from example, an $n^{th}$ image (a preceding image) preceding the first image i1 and an $n^{th}$ image (a following image) following the first image i1, as second images i2 that are to be displayed in second zones z2. Then, the command processor 112 transfers a control command instructing the display unit 200 to display the first image i1 in the first zone z1 and the second images i2 in the second zones z2, to the display unit 200, so that the display unit 200 displays the first image i1 in the first zone z1 and the second images i2 in the second zones z2. For example, when an $123^{rd}$ image included in the first image group c1 is selected, the command processor 112 may generate a control command for displaying an $103^{rd}$ image which is a $20^{th}$ image preceding the selected image in the second zone z2a and an $143^{rd}$ image which is a $20^{th}$ image following the selected image in the second zone z2b together with the $123^{rd}$ image.

Also, the command processor 112 may decide the number of second images i2 that are to be displayed, according to a predetermined setting. For example, when an $123^{rd}$ image is selected as a first image i1, the command processor 112 may decide four images of two preceding images and two following images as second images i2. In this case, the command processor 112 may control the display unit 200 to display an $103^{rd}$ image which is a $20^{th}$ image preceding the first image i1 and a $113^{rd}$ image which is a $10^{th}$ image preceding the first image i1 in a zone located to the left of the first image i1, and to display an $143^{rd}$ image which is a $20^{th}$ image following the first image i1 and a $133^{rd}$ image which is a $10^{th}$ image following the first image i1 in a zone located to the right of the first image i1. As such, the second zones z2 are divided into four sub zones.

Figure 12:
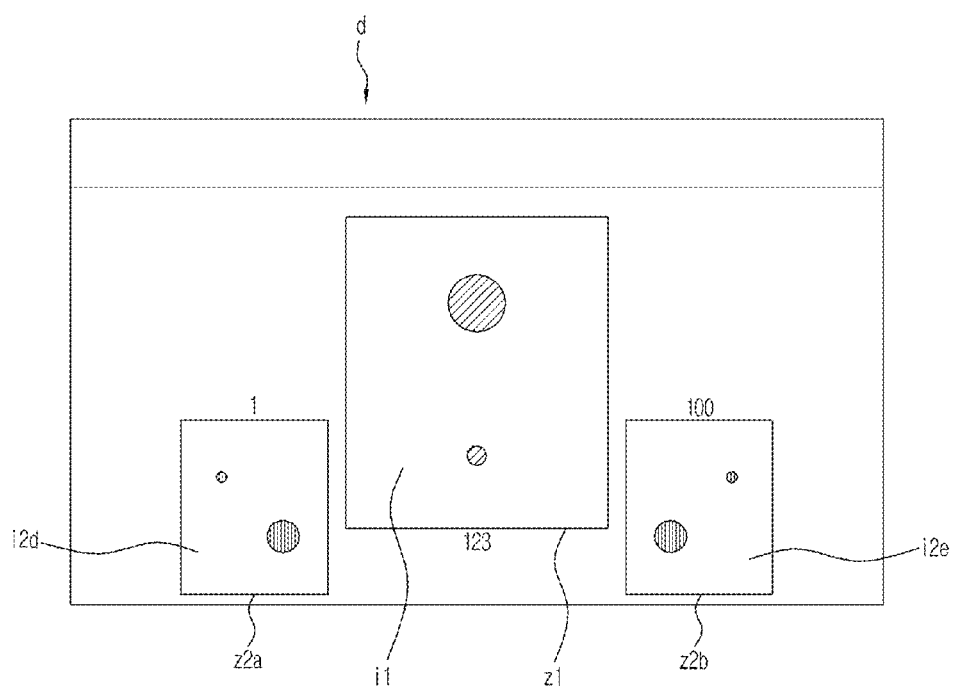
FIGS. 12 to 15 illustrate various screens displayed on a display unit of an ultrasonic imaging apparatus, according to exemplary embodiments of the present invention.

According to one exemplary embodiment, the user may select a first image i1 and second images i2 that are to be displayed in the first zone z1 and the second zones z2, respectively. In this case, the command processor 112 generates a control command for displaying the first image i1 in the first zone z1 and the second images i2 in the second zones z2, according to the user's selection command, and transfers the control command to the display unit 200. FIG. 12 illustrates another exemplary embodiment of a screen displayed on the display unit 200 of the ultrasonic imaging apparatus. Referring to FIG. 12, when first and second images i1 and i2 are images included in a first image group c1, a user may select an $123^{rd}$ image of the first image group c1 as a first image i1, a $1^{st}$ image of the first image group c1 as a second image i2d, and a $170^{th}$ image of the first image group c1 as another second image i2e. In this case, the $1^{st}$ image i2d, the $123^{rd}$ image i1, and the $170^{th}$ image i2e are displayed in a second zone z2a, a first zone z1, and another second zone z2b, respectively.

Also, when a plurality of first images i1 that are to be displayed in the first zone z1 are images belonging to the first image group c1, the command processor 112 may generate a playback control command for playing back the first images i1 according to a user's input command, and transfer the playback control command to the display unit 200. Then, the display unit 200 may sequentially display the first images i1 in the first zone z1 according to the playback control command so that the images i1 of the first image group c1 are played back on the screen.

Also, the command processor 112 may decide operations of the second images i2 according to an operation of the first image i1. For example, when images i1 included in a first image group c1 are being played back on a screen, and second images i2 that are to be displayed on second zones z2 are images included in a second image group c2, the command processor 112 may generate a playback control command for playing back the second images i2 according to the playback operation of the images i1, and transfer the playback control command to the display unit 200. Then, the display unit 200 may sequentially display the second images i2 in the second zones z2 according to the playback control command so that the images i2 of the second image group c2 are played back on the screen. In this case, the first and second image groups c1 and c2 may be the same group or different groups.

As necessary, the command processor 112 may create an appropriate control command based on setting information stored in the setting storage unit 111a.

Figure 13:
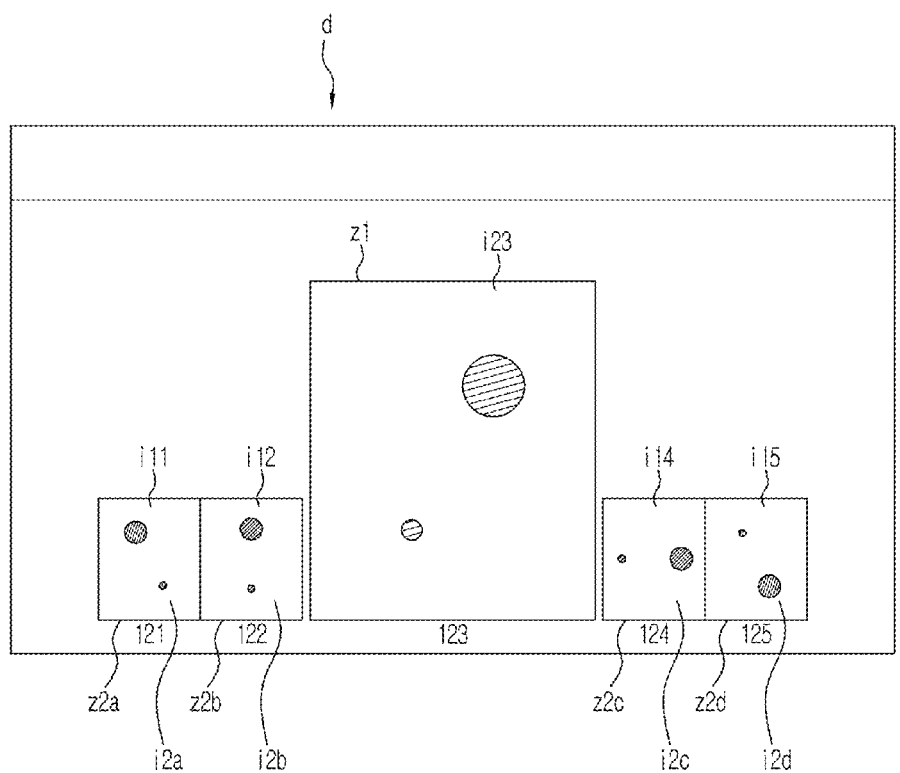
Figure 14:
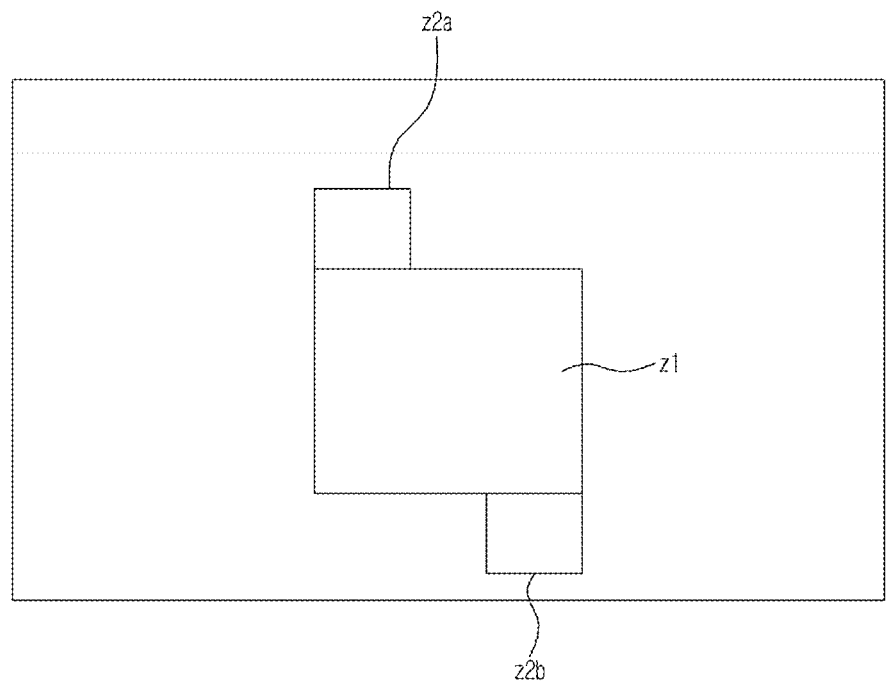
Figure 15:
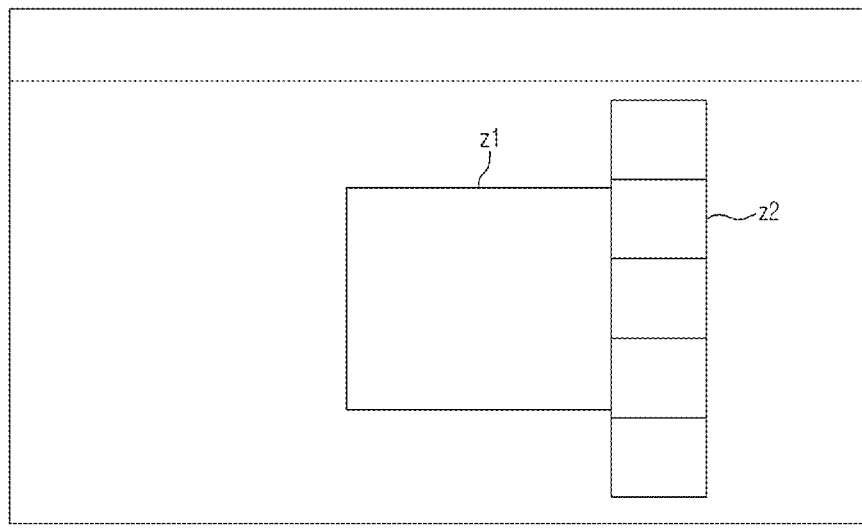

Hereinafter, examples of various screens that are displayed on the display unit 200 according to control operations of the display controller 110 will be described with reference to FIGS. 13, 14, and 15. As illustrated in FIGS. 13, 14, and 15, the display unit 200 may display screens of various layouts according to control operations of the display controller 110.

FIG. 13 illustrates an exemplary embodiment of a screen displayed on the display unit 200 of the ultrasonic imaging apparatus. As illustrated in FIG. 13, second zones z2 may be sub-divided into a plurality of second zones, for example, second zones z2a through z2d.

When at least one first ultrasonic image and at least one second ultrasonic image are ultrasonic image frames belonging to a first image group c, a first zone z1 may display a second ultrasonic image frame i13, and second zones z2a through z2d may display other ultrasonic image frames i11, i12, i14, and i15 having a predetermined relationship with the second ultrasonic image frame i13 displayed in the first zone z1. More specifically, ultrasonic image frames preceding and following the first ultrasonic image frame i13, spaced by a predetermined time period from the first ultrasonic image frame i13 or taken within a predetermined time period from the photographing time of the first ultrasonic image frame i13, for example, image frames just preceding the first ultrasonic image frame i13 and image frames just following the first ultrasonic image frame i13 may be respectively displayed on the second zones z2a through z2d.

Referring to the example of FIG. 13, when an $123^{rd}$ ultrasonic image frame is displayed in the first zone z1, an $121^{st}$ ultrasonic image frame and an $122^{nd}$ ultrasonic image frame just preceding the $123^{rd}$ ultrasonic image frame are displayed in the second zones z2a and the second zone z2b, respectively. Also, a $124^{th}$ ultrasonic image frame and an $125^{th}$ ultrasonic image frame just following the $123^{rd}$ ultrasonic image frame are displayed in the second zones z2c and z2d, respectively. In other words, an ultrasonic image just preceding a displayed ultrasonic image may be displayed to the very left of the displayed ultrasonic image, and an ultrasonic image just following the displayed ultrasonic image may be displayed to the very right of the displayed ultrasonic image. According to one exemplary embodiment, the first zone z1 may be larger than the second zones z2a through z2b, as illustrated in FIG. 13.

FIGS. 14 and 15 illustrate exemplary embodiments of other screens displayed on the display unit 200 of the ultrasonic imaging apparatus. As illustrated in FIG. 14, second zones z2a and z2b may be displayed in the upper and lower parts of a screen. In this case, a preceding ultrasonic image may be displayed in the second zone z2a, and a following ultrasonic image may be displayed in the second zone z2b. Also, as illustrated in FIG. 15, second zones z2 may be arranged only in one side of a screen, for example, to the right of a first zone z1. In this case, a first ultrasonic image displayed in the first zone z1 may be any one of a plurality of ultrasonic images displayed in the second zone 2. A user may select one of ultrasonic images displayed in the second zones z2, and the display controller 110 may control the display unit 200 to display the selected ultrasonic image in the first zone z1. According to one exemplary embodiment, the first ultrasonic image that is displayed on the first zone z1 may be an ultrasonic image located in the center of the second zones z2 among the plurality of ultrasonic images displayed in the second zone z2.

Figure 16:
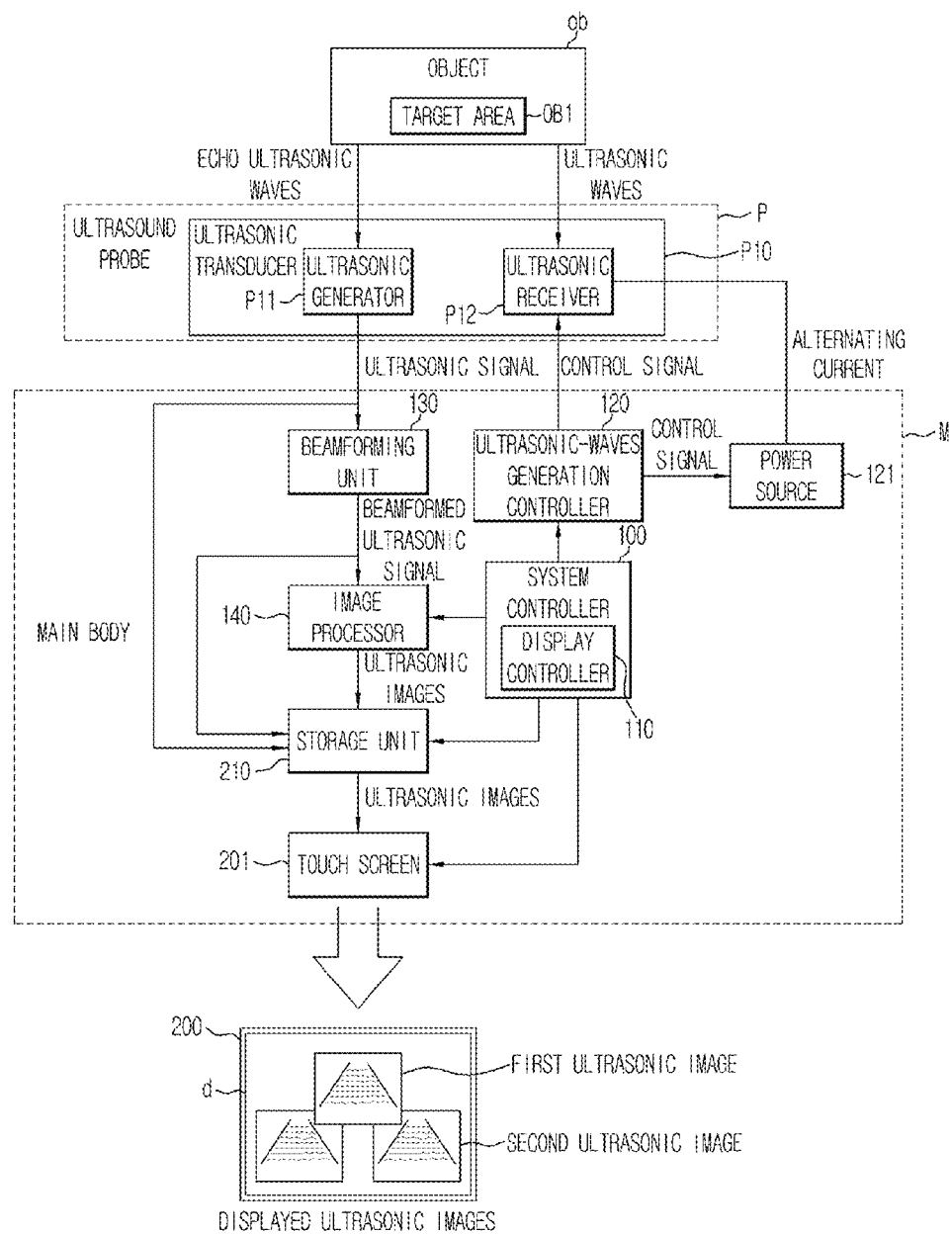
FIG. 16 is a block diagram of an ultrasonic imaging apparatus having a touch screen, according to another exemplary embodiment of the present invention.

FIG. 16 is a block diagram of an ultrasonic imaging apparatus having a touch screen, according to another exemplary embodiment of the present invention. Referring to FIG. 16, the ultrasonic imaging apparatus may include a touch screen 201 instead of the input unit i and the display unit 200 of FIG. 6. The touch screen 201 is a user interface for receiving predetermined commands from a user by sensing touch inputs corresponding to the user's specific gestures.

The touch screen 201 may be a resistive touch screen of detecting pressure to sense a user's touch inputs, a capacitive touch screen of sensing a user's touch inputs using a capacitive coupling effect, or an optical touch screen of sensing external inputs using irradiated light. The screens illustrated in FIGS. 10 to 15 may be displayed on the touch screen 201.

A user can intuitively touch a specific region on the touch screen 201 to select a desired ultrasonic image on a displayed screen. The touch operation may be a single-touch input or a multi-touch input. The touch operation may also include a touch-and-drag input.

Referring to the example of FIG. 15, when second zones z2 are displayed on a screen, a user may tap an ultrasonic image of images displayed in the second zones z2, or touch an ultrasonic image of the images displayed in the second zones z2 and then dragging the ultrasonic image to a first zone z1, thereby selecting an ultrasonic image that is to be displayed on the first zone z1.

Figure 17:
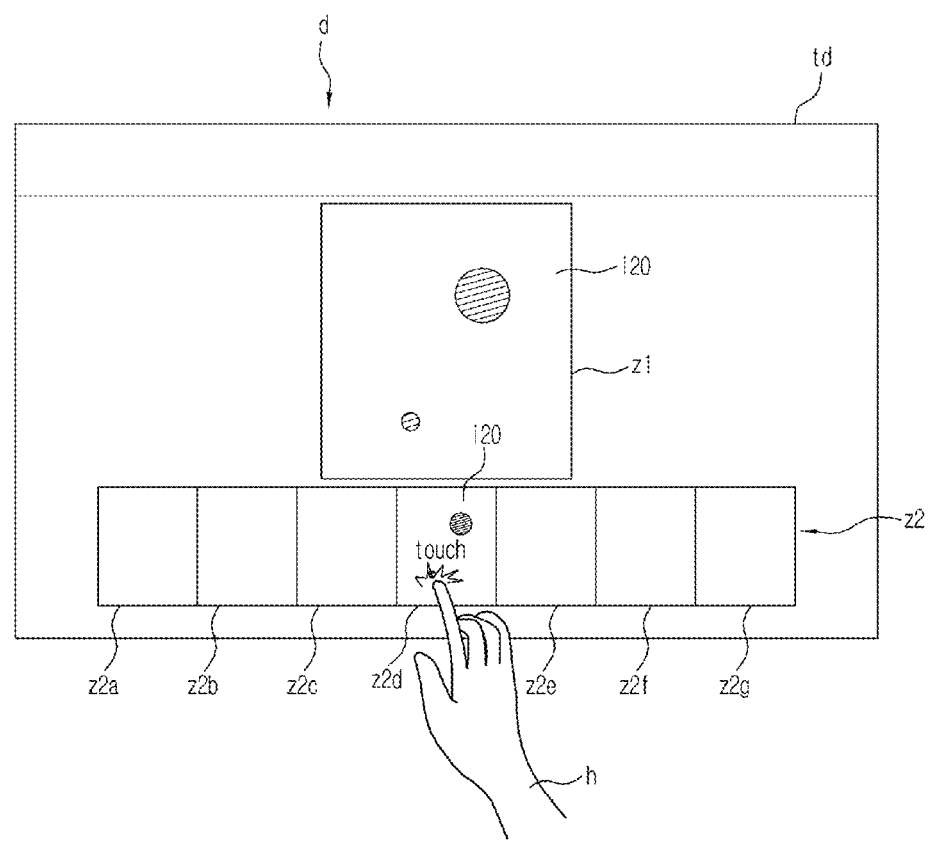
Figure 18:
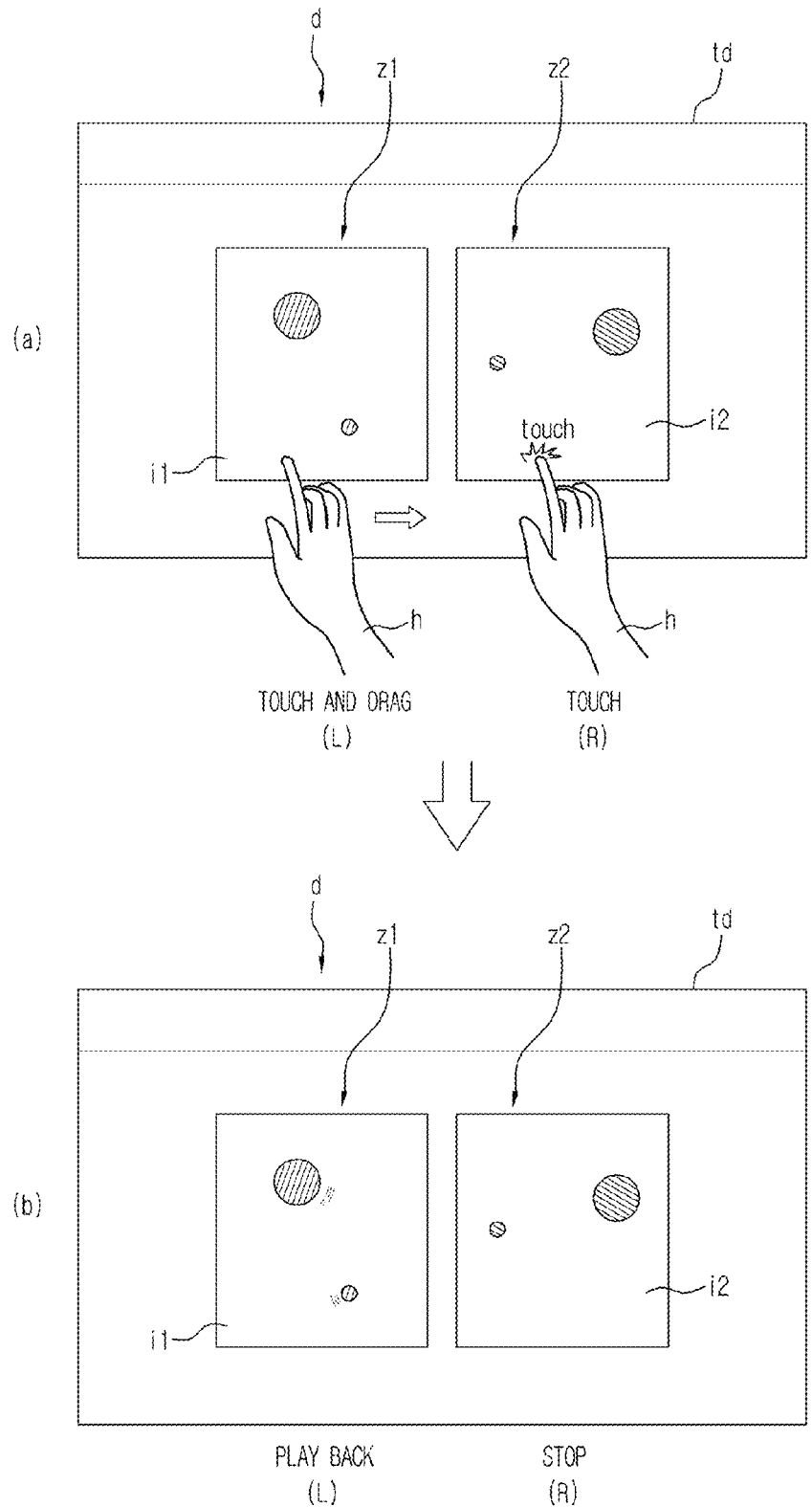
Figure 19:
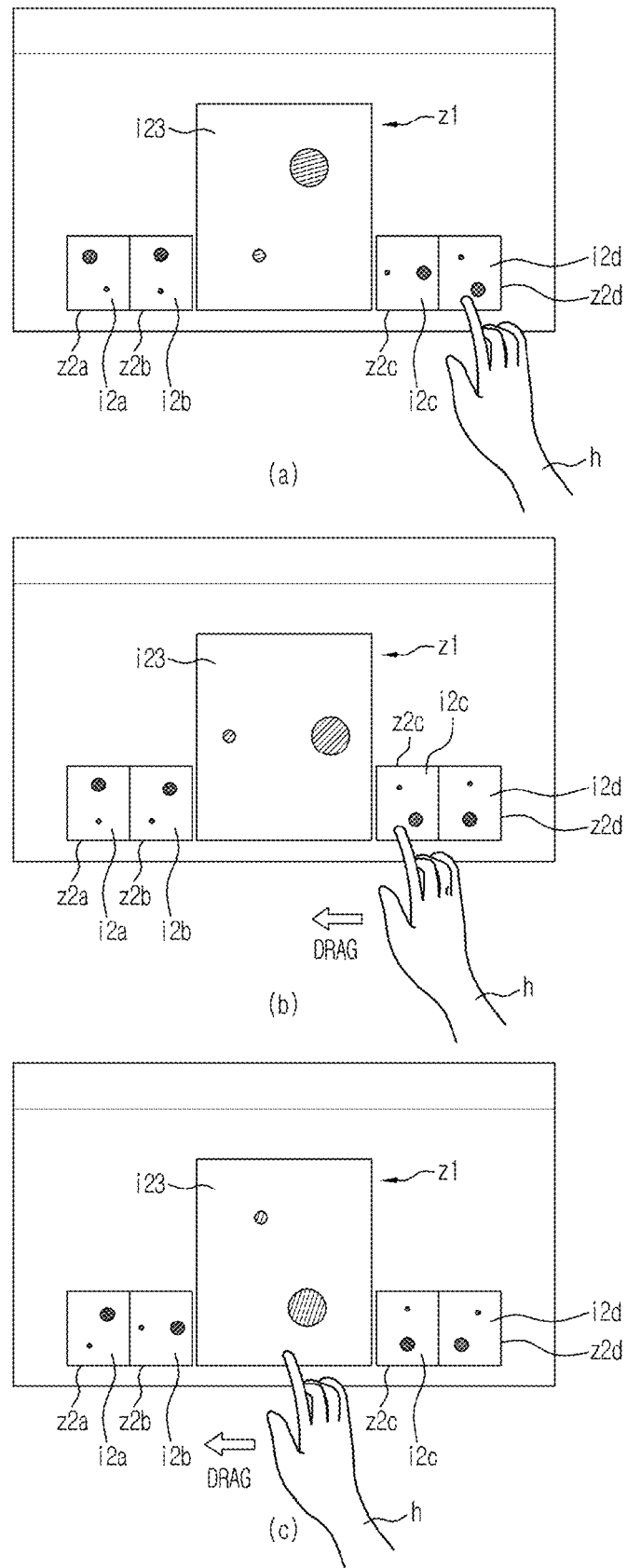

FIGS. 17 to 19 are views for describing various touch inputs for the ultrasonic imaging apparatus having the touch screen 201, according to exemplary embodiments of the present invention.

Referring to FIG. 17, a screen td of the touch screen 201 may include a first zone z1 and at least one second zone z2 arranged below the first zone z1. The second zone z2 may be sub-divided into a plurality of second zones z2a through z2g. When a user touches (for example, taps) one (for example, the second zone z2d) of the second zones z2a through z2g with his/her finger h, the ultrasonic imaging apparatus determines that a second ultrasonic image i20 displayed in the second zone z2d has been selected, and moves the second ultrasonic image i20 to the first zone z1. In this way, the user may select a desired ultrasonic image from among a plurality of second ultrasonic images. Also, in this case, the user may select a desired ultrasonic image using a predetermined gesture such as a multi-touch operation other than tapping.

Referring to FIGS. 18 (a) and (b), a user may touch a specific region on a touch screen td to play back or stop an ultrasound video. For example, it is assumed that ultrasonic videos having images frames corresponding to a plurality of ultrasonic images included in an image group are displayed in a first zone z1 and a second zone z2, respectively, which illustrated in FIG. 18(a). As illustrated in the left part "L" of FIG. 18(a), when a user touches the first zone z1 and then drags the first zone z1 by a predetermined distance, the ultrasound video displayed in the first zone z1 is played back. Meanwhile, as illustrated in the right part "R" of FIG. 18(a), if the user touches the second zone z2 when the ultrasound video displayed in the second zone z2 is being played back, the ultrasound video is stopped, which is illustrated in FIG. 18(b). As such, the ultrasonic videos displayed in the first and second zones z1 and z2 operate in different ways depending on a user's touch inputs.

Referring to FIG. 19, a user may touch the touch screen 201 to display a specific ultrasonic image in a first zone z1. As illustrated in FIG. 19(a), the first zone z1 is positioned in the center of a display screen of the touch screen 201. A second zone z2 is divided into a plurality of second zones z2a through z2d, and the plurality of second zones z2a through z2d are arranged in both sides of the first zone z1. As a result, as illustrated in FIG. 19, the second zone z2a, the second zone z2b, the first zone z1, the second zone z2c, and the second zone z2d are arranged in this order from left to right. The individual zones z2a, z2b, z1, z2c, and z2d display predetermined ultrasonic images i21 through i25.

In this case, as illustrated in FIGS. 19(a) and 19(b), if a user touches the second zone z2d with his/her finger h and drags his/her finger to the left, all the ultrasonic images i21 through i25 displayed in the zones z2a, z2b, z1, z2c, and z2d are shifted to the left. That is, the ultrasonic image i25 having displayed in the second zone z2d moves to the second zone z2c, and the ultrasonic image i24 having displayed in the second zone z2c moves to the first zone z1. Also, the ultrasonic image i23 having displayed in the first zone z1 moves to the second zone z2b. Meanwhile, the second zone z2d displays a new ultrasonic image i26. If the user continues to drag his/her finger h to the left until his/her finger arrives at the first zone z1, the ultrasonic image i25 initially having displayed in the second zone z2d moves to the first zone z1. That is, ultrasonic images move according to a user finger's movement.

It is assumed that a first image is a first image frame which is one of a plurality of image frames included in at least one image group, and second images are second image frames belonging to the same image group to which the first image frame belongs. In this case, the second image frames that are to be displayed in second zones (for example, the second zones z2a and z2b of FIG. 10) may be decided according to a user's touch input (for example, a multi-touch input) to the touch screen 201. As illustrated in FIG. 20(a), when a user touches the touch screen 201 with his/her two fingers h1 and h2 and then spreads his/her fingers h1 and h2 side to side, different image frames preceding and following the first image frame, having longer frame intervals with respect to the first image, may be displayed in the second zones z2a and z2b, respectively.

More specifically, as illustrated in FIG. 20(a), it is assumed that an $123^{rd}$ image frame is displayed in a first zone z1, an $103^{rd}$ image frame is displayed in a second zone z2a, and an $143^{rd}$ image frame is displayed in another second zone z2b. In this case, when a user touches the touch screen 201 with his/her two fingers h1 and h2 and then spreads his/her fingers h1 and h2 side to side, the $103^{rd}$ image frame displayed in the second zone z2a changes to another image frame having a longer frame interval with respect to the $123^{rd}$ image frame, and the $143^{rd}$ image frame displayed in the second zone z2b also changes to another image frame having a longer frame interval with respect to the $123^{rd}$ image frame. Accordingly, as illustrated in FIG. 20(*b*), an $83^{rd}$ image frame may be displayed in the second zone z2a, and an $163^{rd}$ image frame may be displayed in the second zone z2b. In this way, the frame intervals between a plurality of displayed image frames may be adjusted.

(3) Hereinafter, various exemplary embodiments of image display methods will be described with reference to FIGS. 21 to 24. FIGS. 21 to 24 are flowcharts of image display methods according to exemplary embodiments of the present invention.

Figure 21:
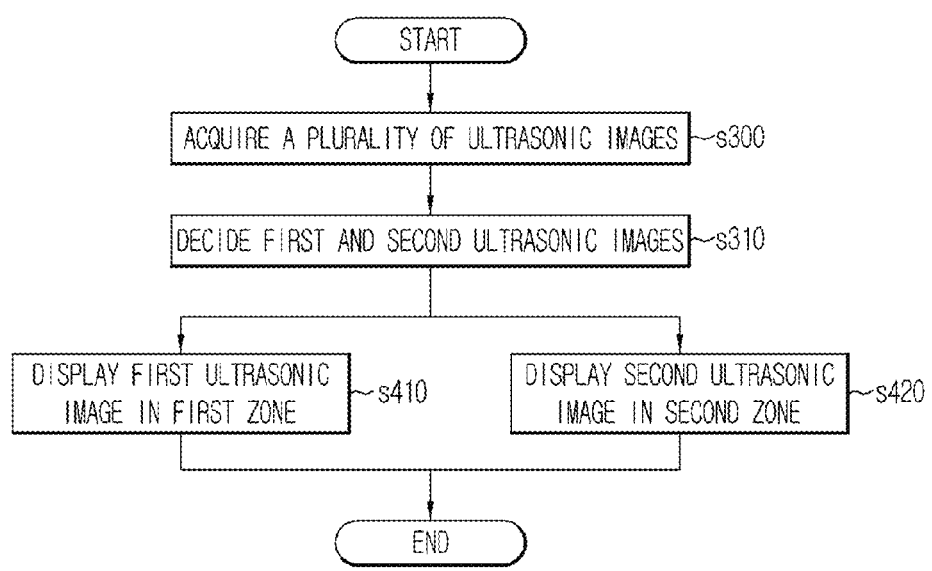
FIGS. 21 to 23 are flowcharts of image display methods according to exemplary embodiments of the present invention.

Referring to an image display method of an ultrasonic imaging apparatus as illustrated in FIG. 21, an ultrasonic imaging apparatus radiates ultrasonic waves to an object, collects ultrasonic waves reflected from a target area of the object, and then performs beamforming and image processing to thus acquire a plurality of ultrasonic images (s300). The plurality of ultrasonic images may be ultrasonic still images or ultrasonic moving images. Then, the ultrasonic imaging apparatus decides a first ultrasonic image and a second ultrasonic image according to a user's selection or a predetermined setting (s310). At this time, any one of first and second ultrasonic images may be decided by a user, and the other one may be decided by the ultrasonic imaging apparatus. Then, the ultrasonic imaging apparatus displays the decided ultrasonic images in the corresponding zones on a screen of a display unit. More specifically, the ultrasonic imaging apparatus may display the first ultrasonic image in a first zone (s410) and the second ultrasonic image in a second zone (s420). Here, each of the first and second zones may be a plurality of zones. Also, as described above with reference to FIG. 10, the first and second zones may be arranged with various sizes in various layouts on a screen. When the first or second ultrasonic image is a video, the first or second ultrasonic image may be independently played back.

Figure 22:
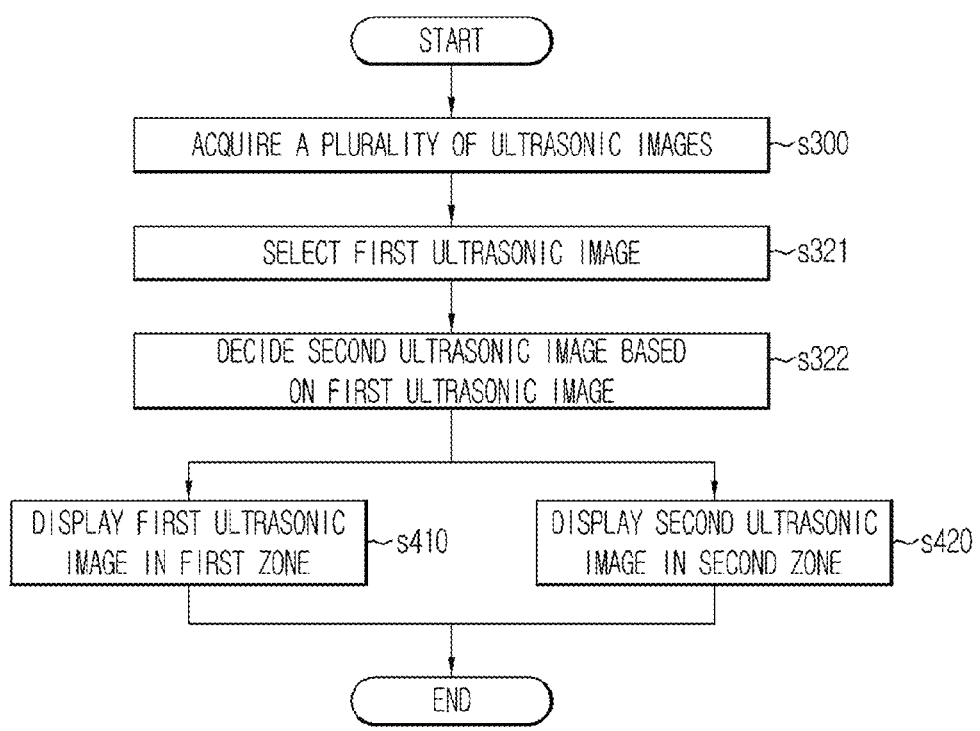

Now, referring to an image display method of an ultrasonic imaging apparatus as illustrated in FIG. 22, an ultrasonic imaging apparatus acquires a plurality of ultrasonic images in the same way or by the same method as described above with reference to FIG. 21 (s300). Then, the ultrasonic imaging apparatus selects at least one first ultrasonic image according to a user's selection or a predetermined setting (s321), and decides at least one second ultrasonic image based on the first ultrasonic image (s322). At this time, the ultrasonic imaging apparatus may select at least one ultrasonic image taken within a predetermined time period from the photographing time of the first ultrasonic image, as a second ultrasonic image. For example, when the first ultrasonic image belongs to one of a plurality of image groups, an ultrasonic image preceding the first ultrasonic image by a predetermined frame interval, or by a predetermined number of frames, may be selected as one second ultrasonic image, and an ultrasonic image following the first ultrasonic image with the predetermined frame interval may be selected as another second ultrasonic image. Then, the ultrasonic imaging apparatus may display the first and second ultrasonic images in the corresponding zones of a display unit (s410 and s420).

Figure 23:
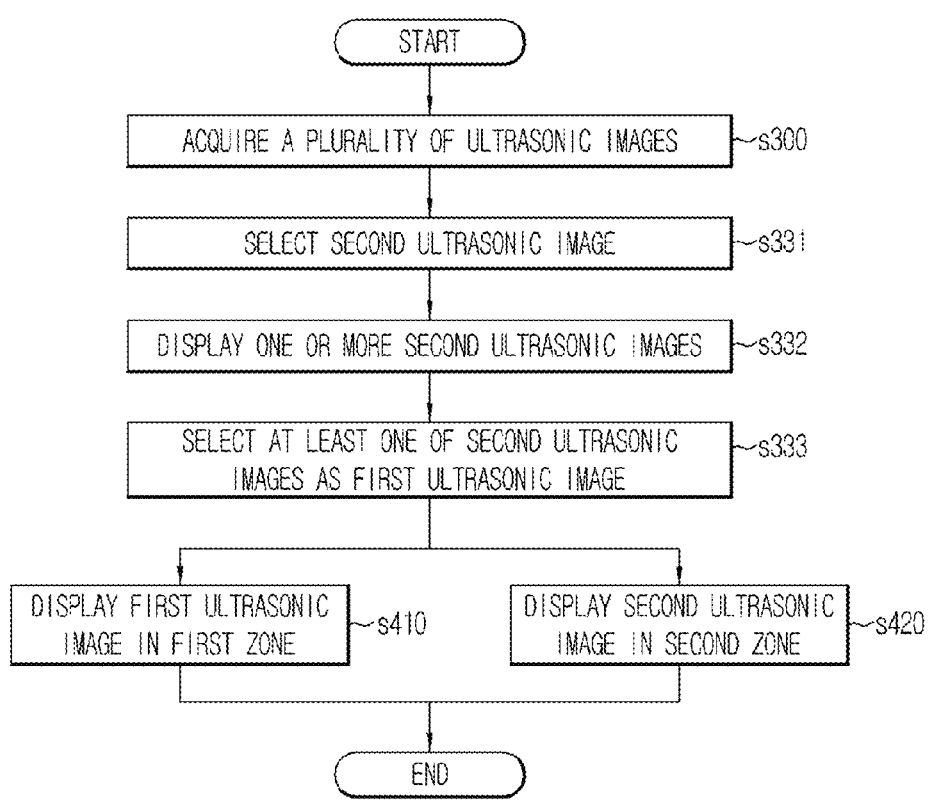

Referring to an image display method of an ultrasonic imaging apparatus as illustrated in FIG. 23, an ultrasonic imaging apparatus acquires a plurality of ultrasonic images by the same method as described above with reference to FIG. 21 (s300). Then, the ultrasonic imaging apparatus decides one or more second ultrasonic images that are to be displayed from among the plurality of ultrasonic images (s331), and displays the decided second ultrasonic images on a screen of a display unit (s332). Thereafter, if a user manipulates an input unit or touches a touch screen to select at least one ultrasonic image of the second ultrasonic images as a first ultrasonic image (s333), the ultrasonic imaging apparatus displays the first and second ultrasonic images in the corresponding zones of the screen (s410 and s420).

In the above description, for convenience of description, exemplary embodiments in which the image display apparatus and method according to the present invention are applied to an ultrasonic imaging apparatus have been provided, however, the image display apparatus and method can be applied to Digital Radiography (DR) or Computed Tomography (CT) in the same manner or through appropriate modifications. For example, the DR radiates X-rays to a target through an X-ray irradiator, detects X-rays that have penetrated the target or are reflected from the target by an X-ray detector, and acquires an X-ray image based on the detected X-rays. The DR may acquire a plurality of X-ray images by radiating X-rays several times or performing image processing. The acquired X-ray images are displayed on a screen of a display unit installed in the DR or connected to the DR through a wired/wireless communication network. When the X-ray images are displayed on the screen, at least one X-ray image may be displayed in a part of the screen, and one or more different X-ray images may be displayed in the other part of the screen. In this case, the screen of the display unit may display images similar to the ones illustrated in FIG. 10. When the display unit is a touch screen, a user can decide a format of X-ray images that are to be displayed or a relationship between X-ray images that are to be displayed, through a single-touch or a multi-touch operation. The image display apparatus and method according to the present invention may also be applied to CT in the same manner.

Although a few embodiments of the present invention have been shown and described, it would be appreciated by those skilled in the art that changes may be made in these embodiments without departing from the principles and spirit of the invention, the scope of which is defined in the claims and their equivalents.

In addition, many modifications can be made to adapt a particular situation or material to the teachings of the present disclosure without departing from the essential scope thereof. Therefore, it is intended that the present disclosure not be limited to the particular exemplary embodiments disclosed as the best mode contemplated for carrying out the present disclosure, but that the present disclosure will include all embodiments falling within the scope of the appended claims.

What is claimed is:

1. An ultrasonic imaging apparatus comprising:
a display unit; and
a controller configured to control the display unit to display:
  a first set of ultrasonic images comprising at least one first image of a plurality of images to be displayed in a first zone of a screen of the display unit, and
  a second set of ultrasonic images comprising at least one second image of the plurality of images to be displayed in a second zone of the screen of the display unit,
wherein the first set of ultrasonic images corresponds to a first scanning of a target area which is performed by the ultrasonic imaging apparatus at a first time, and the second set of ultrasonic images corresponds to a second scanning of the target area which is performed by the ultrasonic imaging apparatus at a second time, wherein the plurality of images comprises a plurality of image frames classified into one or more image groups, wherein the first image comprises a first image frame, and the second image comprises a second image frame, wherein the first image frame and the second image frame are image frames belonging to different image groups.

2. The ultrasonic imaging apparatus according to claim 1, wherein:

the second image is an image selected according to the first image, or the first image is an image selected according to the second image.

3. The ultrasonic imaging apparatus according to claim 1, further comprising an input unit receiving a selection command for selecting the first image or the second image from an user or an external device.

4. The ultrasonic imaging apparatus according to claim 3, wherein the input unit receives a selection command for selecting the first image or the second image from among the plurality of images.

5. The ultrasonic imaging apparatus according to claim 3, wherein:

the input unit receives a selection command for selecting the at least one second image from the first set of ultrasonic images comprising the at least one first image, or a selection command for selecting the at least one first image from the second set of ultrasonic images comprising the at least one second image.

6. The ultrasonic imaging apparatus according to claim 1, wherein:

the first image is an image of the second set of ultrasonic images, or the second image is an image of the first set of ultrasonic images.

7. The ultrasonic imaging apparatus according to claim 1, wherein the first image frame and the second image frame are image frames belonging to the same image group.

8. The ultrasonic imaging apparatus according to claim 7, wherein:

the first image frame and the second image frame are comprised in a ordered sequence of frames;

the second image frame is preceding the first image frame in the sequence of frames or the second image frame is following the first image frame in the sequence of frames.

9. The ultrasonic imaging apparatus according to claim 8, wherein a predetermined number of preceding image frames or a predetermined number of following image frames are displayed in the second zone of the screen of the display unit.

10. The ultrasonic imaging apparatus according to claim 8, wherein the second image frame is disposed in the sequence of frames within a predetermined frame interval or a predetermined number of frames from the first image frame.

11. The ultrasonic imaging apparatus according to claim 1, wherein the first image frame and the second image frame are image frames belonging to different image groups.

12. The ultrasonic imaging apparatus according to claim 1, wherein: if the first zone displays a first video as a sequence of frames comprising the first image frame, then the second zone displays a second video as a sequence of frames comprising the second image frame and the second video is displayed in relation to the first video, or if the second zone displays a second video as a sequence of frames comprising the second image frame, then the first zone displays a first video as a sequence of frames comprising the first image frame and the first video is displayed in relation to the second video.

13. The ultrasonic imaging apparatus according to claim 1, wherein the display unit is a touch screen receiving an external command according to a user's touch operation.

14. The ultrasonic imaging apparatus according to claim 13, wherein at least one of the first image and the second image is selected according to a user's gesture input to the touch screen.

15. The ultrasonic imaging apparatus according to claim 13, wherein at least one of a first image and a second image, displayed in a first zone on the touch screen or in the second zone on the touch screen, changes according to a user's gesture input to the touch screen.

16. The ultrasonic imaging apparatus according to claim 13, wherein at least one of a first image and a second image, displayed in the first zone on the touch screen or in the second zone on the touch screen, is a still image according to a user's gesture input to the touch screen.

17. The ultrasonic imaging apparatus according to claim 13, wherein:

when the first image changes according to a touch operation input to the touch screen, the second image changes in correspondence to the change of the first image, or when the second image changes according to a touch operation input to the touch screen, the first image changes in correspondence to the change of the second image.

18. The ultrasonic imaging apparatus according to claim 13, wherein:

the plurality of images are a plurality of image frames classified into at least one image group, the first image is a first image frame, the second image is a second image frame, and a frame interval or a number of frames between the first image frame and the second image frame, in a sequence of frames comprising the first image frame and the second image frame, is selected according to a touch operation input to the touch screen.

19. The ultrasonic imaging apparatus according to claim 1, wherein the first scanning of the target area is performed by the ultrasonic imaging apparatus prior to an injection of a contrast medium into the target area, and the second scanning of the target area is performed by the ultrasonic imaging apparatus after the injection of the contrast medium into the target area.

20. An X-ray imaging apparatus comprising:

a display unit; and a controller configured to control the display unit to display at least one first X-ray image of a plurality of images to be displayed in a first zone of a screen of the display unit, and at least one second X-ray image of the plurality of images to be displayed in a second zone of the screen of the display unit, wherein the at least one first X-ray image corresponds to a first scanning of a target area which is performed by the X-ray imaging apparatus at a first time, and the at least one second X-ray image corresponds to a second scanning of the target area which is performed by the X-ray imaging apparatus at a second time, wherein the plurality of images comprises a plurality of image frames classified into one or more image groups, wherein the first image comprises a first image frame, and the second image comprises a second image frame, wherein the first image frame and the second image frame are image frames belonging to different image groups.

21. A method of displaying ultrasonic images, the method comprising:

acquiring a plurality of images;

selecting at least one first ultrasonic image and at least one second ultrasonic image from the plurality of images, wherein the plurality of images comprises a plurality of image frames classified into one or more image groups, the first image comprises a first image frame, and the second image comprises a second image frame;

displaying the at least one first ultrasonic image in a first zone of a display screen, and the at least one second ultrasonic image in a second zone of the display screen; and changing the second image frame in correspondence with a change of the first image frame, or changing the first image frame in correspondence with a change of the second image frame, wherein the at least one first ultrasonic image corresponds to a first scanning of a target area which is performed by an ultrasonic imaging apparatus at a first time, and the at least one second ultrasonic image corresponds to a second scanning of the target area which is performed by the ultrasonic imaging apparatus at a second time.

22. The method of displaying ultrasonic images according to claim 21, wherein the selecting of the first ultrasonic image and the second ultrasonic image comprises:

selecting the at least one first ultrasonic image from among the plurality of images; and selecting the at least one second ultrasonic image based on the at least one first ultrasonic image selected from among the plurality of images.

23. The method of displaying ultrasonic images according to claim 21, wherein the at least one second ultrasonic image is different from the at least one first ultrasonic image.

24. The method of displaying ultrasonic images according to claim 21, wherein, in a sequence of frames comprising the first ultrasonic image and the second ultrasonic image, the second ultrasonic image is a preceding image preceding the first ultrasonic image or a following image following the first ultrasonic image.

* * * * *